United States Patent
Gack et al.

(10) Patent No.: US 7,842,464 B2
(45) Date of Patent: Nov. 30, 2010

(54) USE OF ADAM 12 FOR DIAGNOSIS AND THERAPY OF PREECLAMPSIA

(75) Inventors: Sabine Gack, Plankstadt (DE); Marina Schorpp-Kistner, Durmersheim (DE); Peter Angel, Dossenheim (DE); Gunnar Wrobel, Heidelberg (DE); Peter Lichter, Gaiberg (DE); Alexander Marme, Heidelberg (DE); Susanne Stumm, Leimen (DE)

(73) Assignee: DKFZ Deutsches Krebsforschungszentrum, Heidelberg (DE)

( * ) Notice: Subject to any disclaimer, the term of this patent is extended or adjusted under 35 U.S.C. 154(b) by 516 days.

(21) Appl. No.: 10/576,266

(22) PCT Filed: Oct. 15, 2004

(86) PCT No.: PCT/EP2004/011632
§ 371 (c)(1),
(2), (4) Date: Dec. 20, 2006

(87) PCT Pub. No.: WO2005/040831
PCT Pub. Date: May 6, 2005

(65) Prior Publication Data
US 2007/0161548 A1 Jul. 12, 2007

(30) Foreign Application Priority Data
Oct. 17, 2003 (EP) .................................. 03023815

(51) Int. Cl.
*G01N 33/53* (2006.01)
(52) U.S. Cl. ...................................................... 435/7.1
(58) Field of Classification Search ........................ None
See application file for complete search history.

(56) References Cited

U.S. PATENT DOCUMENTS

| | | | |
|---|---|---|---|
| 5,744,305 A | 4/1998 | Fodor et al. | |
| 2003/0170627 A1 | 9/2003 | Walker et al. | |
| 2004/0002467 A1 | 1/2004 | Ward et al. | |
| 2006/0134654 A1* | 6/2006 | Wewer et al. | ................... 435/6 |
| 2008/0292619 A1* | 11/2008 | Sehara et al. | ............. 424/133.1 |

FOREIGN PATENT DOCUMENTS

| | | |
|---|---|---|
| WO | WO 99/46597 | 9/1999 |
| WO | WO 03/020220 A2 | 3/2003 |

OTHER PUBLICATIONS

Laigaard et al. ADAM12: a novel first-trimester maternal serum marker for Down syndrome. Prenat Diagn. Dec. 30, 2003;23(13):1086-91.*
Christiansen et al (2007): ADAM12 as a second-trimester maternal serum marker in screening for Down syndrome. Prenat Diagn 27, 611-615.*
Wewer et al. ADAM12 is a four-leafed clover: the excised prodomain remains bound to the mature enzyme. J Biol Chem. 281(14)9418-9422, 2006.*
Attwood TK. Genomics. The Babel of bioinformatics. Science. 290(5491):471-473, 2000.*
Skolnick et al. From genes to protein structure and function: novel applications of computational approaches in the genomic era. Trends Biotechnol. 18(1):34-9, 2000.*
Barton et al. Semin. Gastrointestinal complications of pre-eclampsia. Perinatol. Jun. 2009;33(3):179-88.*
Beaulieu, Canadian Guide to Clinical Preventive Health Care, Ottawa: Health Canada, 1994, 136-43.
Maniatis et al., Molecular Cloning: A Laboratory Manual, Cold Spring Harbor Lab, Cold Spring Harbor, NY, 1989, 16 pgs.
Altschul et al., Nucleic Acids Res., 25:3389-3402.
Feinberg, A.P. and Vogelstein, B. (1983), Anal. Biochem. 132:6-13.
Seals, D.F., and Courtneidge, S.A., the ADAMs Family of Metalloproteases: Multidomain Proteins with Multiple Functions, Genes & Dev. 17, 7-30, 2003.
Ng, E.K.O., Tsui, N.B.Y., et al., Proc. Natl. Acad. Sci. USA, 2003, vol. 100(8): 4748-53.
Shi et al., L.J. (2000), J. Biol. Chem. 275, 18574-18580.
Gilpin, B.J. et al., Journal of Biological Chemistry, vol. 273, No. 1 (1998) pp. 157-166.
Mizutani, S., Akiyama, H. Kurauchi, O., et al., (1985), Arch. Gynecol. 236(3): 165-72.
Tempfer, C.B., Bancher-Todesca, D., Zeisler, H., et al., 2000, Placental Expression and Serum Concentrations of Cytokeratin 19 in Preeclampsia, Obstet. Gynecol. 95(5): 677-82.
Miyawaki, A., Tsien, Methods Enzymol. 2000, vol. 327, pp. 472-500.
Tuschl, Nature Biotechnology, vol. 20, pp. 446-448.
Kolben M., et al., European Journal of Obstetrics, (1996), vol. 68, No. 1-2, pp. 59-65.
Masanori Asakura et al.: Nature Medicine, vol. 8, No. 1 (2002), pp. 35-40.
Pang Z. J. et al., British Journal of Biomedical Science, vol. 60, No. 2 (2003), pp. 97-101.
Database WPI, Derwent Publications Ltd., (1986). SU19853857363 Reznikov et al. Prognosis of pathological pregnancy—by measurign blood alpha-macroglobulin content for early predication of spontaneous abortion or pregnancy toxicosis. p. 1.
Leach R. E. et al., Lancet, vol. 360, No. 9341 (2002), pp. 1215-1219.
Schroeder, Barrett M., America Family Physician Practice Guidelines—AGOG Practice Bulletin on Diagnosing and Managing Preeclampisa and Eclampia, Jul. 15, 2002; available at http://www.aafp.org/afp/2002715/practice.html.
Hofmeyr, et al. BMC Medicine, 2009 (7)11; available at http://www.biomedcentral.com/1741-7015/7/11.
Merck Manual, Abnormalities of Pregnancy: Preeclampsia and Eclampsia (last full review/revision Nov. 2005; content last modified Nov. 2005); available at http://www.merck.com/mmpe/sec18/ch263/ch263j.html.

* cited by examiner

*Primary Examiner*—Maher M Haddad
(74) *Attorney, Agent, or Firm*—Foley & Lardner LLP

(57) ABSTRACT

The present invention relates to the significant role of ADAM 12, ADAM 12-L, and ADAM 12-S in preeclampsia and related disorders. The invention further relates to the use of said genes and gene products, ligands binding to those, and modulators of activity of the gene products in diagnosis and treatment of preeclampsia and related syndromes. The invention also relates to the use of further genes and combinations thereof in diagnosis of preeclampsia and related syndromes.

4 Claims, 8 Drawing Sheets

A

| Pat. No. | GA | Ctrl. | Preecl. |
|---|---|---|---|
| 5 | 38+2 | + | - |
| 6 | 37+2 | + | - |
| 20 | 34 | + | - |
| 21 | 41+3 | + | - |
| 14 | 38+2 | - | + |
| 16 | 33+2 | - | + |
| 22 | 35+1 | - | + |

B

Fig. 4
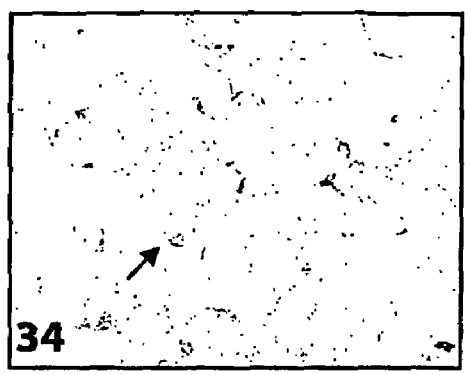 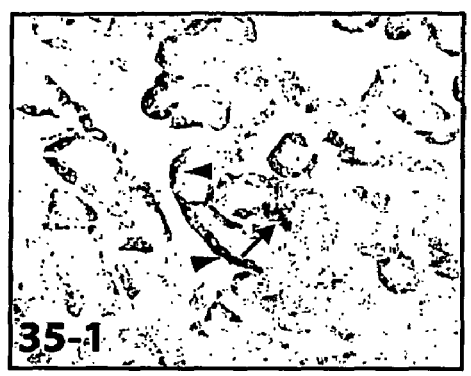
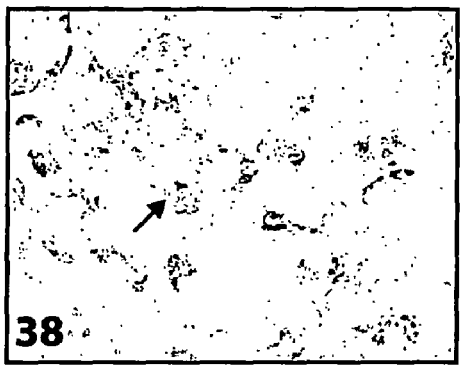 

Fig. 5
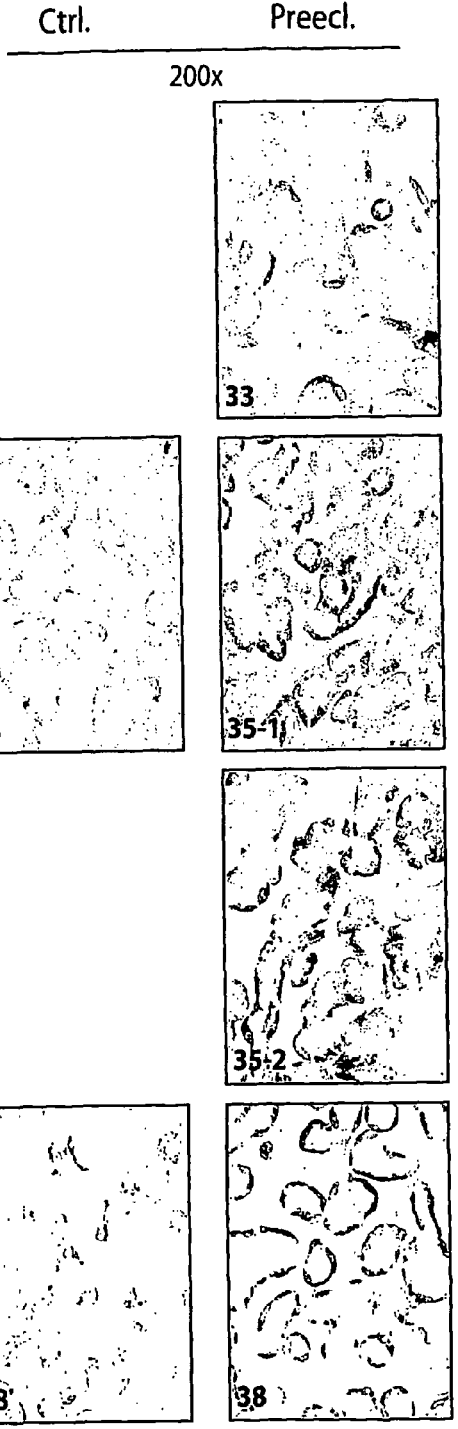

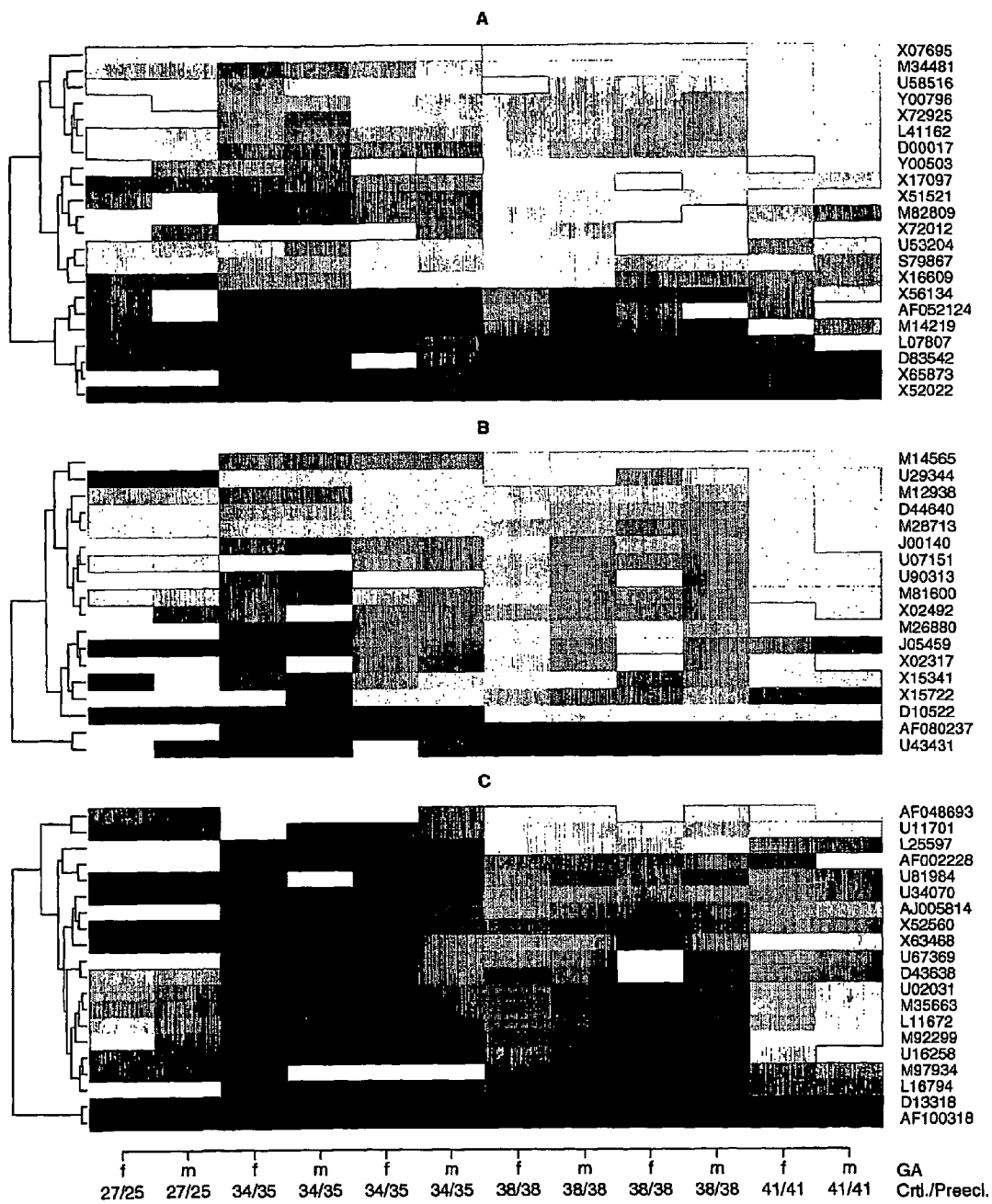
Fig.6 (1/2)

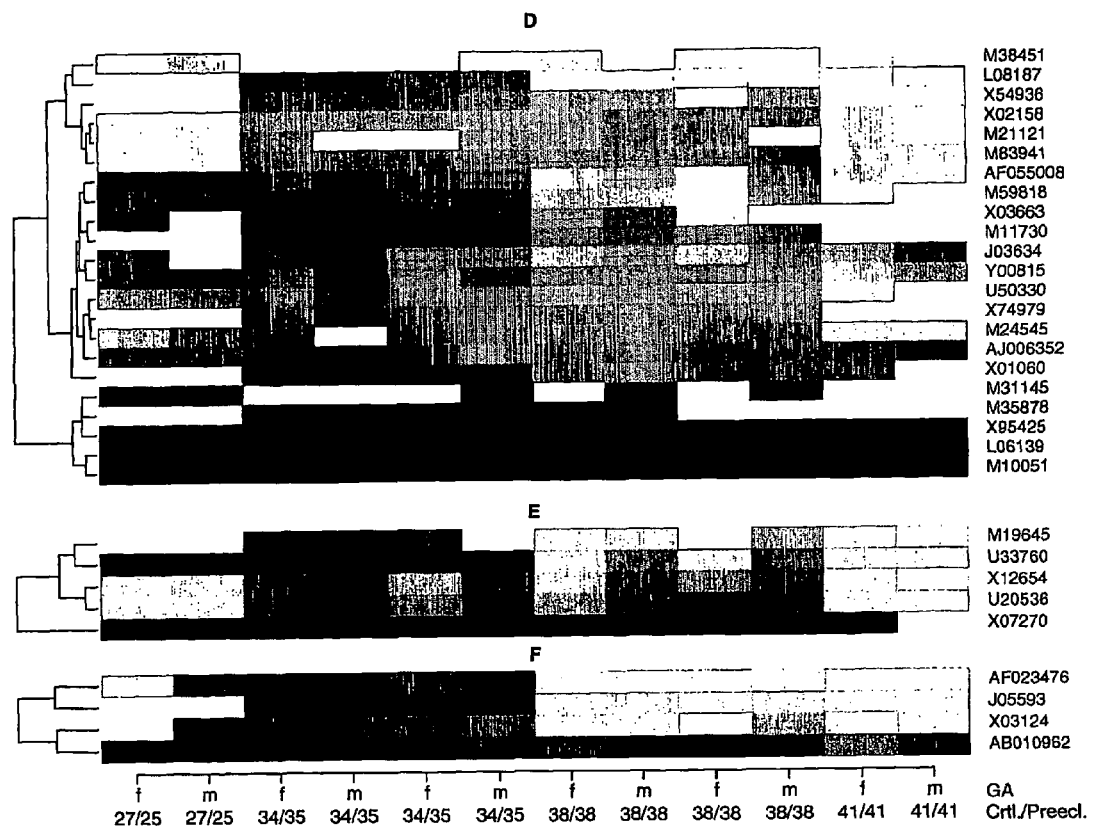
Fig.6 (2/2)

Fig. 7
A
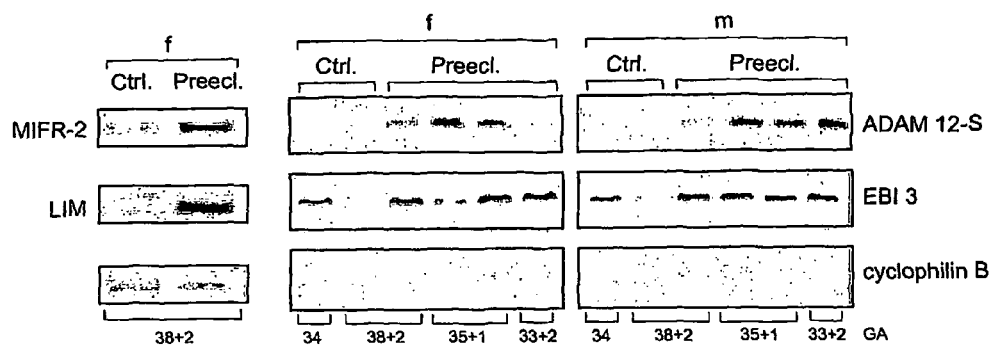
B
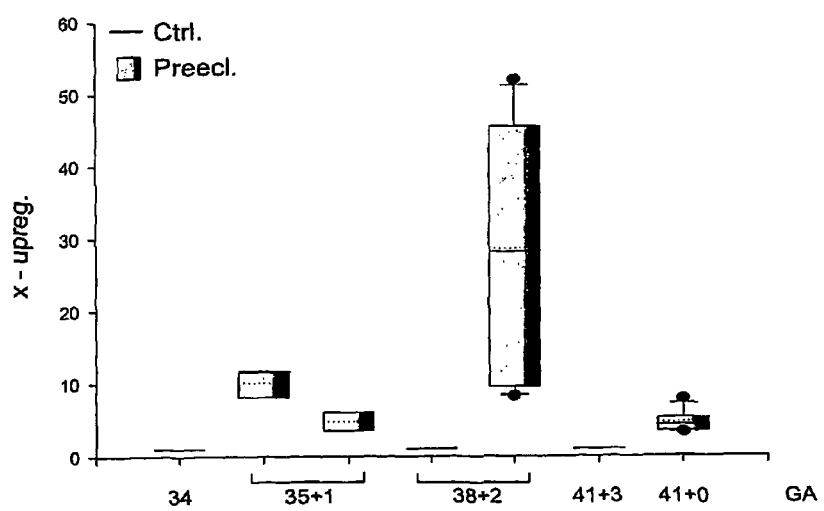

SEQUENCE LISTING

```
<160> NUMBER OF SEQ ID NOS: 20

<210> SEQ ID NO 1
<211> LENGTH: 5062
<212> TYPE: DNA
<213> ORGANISM: Homo sapiens
<220> FEATURE:
<221> NAME/KEY: CDS
<222> LOCATION: (307)..(3036)
<223> OTHER INFORMATION:

<400> SEQUENCE: 1
cactaacgct cttcctagtc cccgggccaa ctcggacagt ttgctcattt attgcaacgg      60
tcaaggctgg cttgtgccag aacggcgcgc gcgcgacgca cgcacacaca cggggggaaa     120 ctttttaaa aatgaaaggc tagaagagct cagcggcggc gcgggccgtg cgcgagggct     180
ccggagctga ctcgccgagg caggaaatcc ctccggtcgc gacgcccggc cccgctcggc     240
gcccgcgtgg gatggtgcag cgctcgccgc cgggcccgag agctgctgca ctgaaggccg     300 gcgacg atg gca gcg cgc ccg ctg ccc gtg tcc ccc gcc cgc gcc ctc        348
        Met Ala Ala Arg Pro Leu Pro Val Ser Pro Ala Arg Ala Leu
        1               5                   10 ctg ctc gcc ctg gcc ggt gct ctg ctc gcg ccc tgc gag gcc cga ggg       396
Leu Leu Ala Leu Ala Gly Ala Leu Leu Ala Pro Cys Glu Ala Arg Gly
15                  20                  25                  30 gtg agc tta tgg aac caa gga aga gct gat gaa gtt gtc agt gcc tct       444
Val Ser Leu Trp Asn Gln Gly Arg Ala Asp Glu Val Val Ser Ala Ser
                35                  40                  45 gtt cgg agt ggg gac ctc tgg atc cca gtg aag agc ttc gac tcc aag       492
Val Arg Ser Gly Asp Leu Trp Ile Pro Val Lys Ser Phe Asp Ser Lys
            50                  55                  60 aat cat cca gaa gtg ctg aat att cga cta caa cgg gaa agc aaa gaa       540
Asn His Pro Glu Val Leu Asn Ile Arg Leu Gln Arg Glu Ser Lys Glu
65                  70                  75 ctg atc ata aat ctg gaa aga aat gaa ggt ctc att gcc agc agt ttc       588
Leu Ile Ile Asn Leu Glu Arg Asn Glu Gly Leu Ile Ala Ser Ser Phe
        80                  85                  90 acg gaa acc cac tat ctg caa gac ggt act gat gtc tcc ctc gct cga       636
Thr Glu Thr His Tyr Leu Gln Asp Gly Thr Asp Val Ser Leu Ala Arg
95                  100                 105                 110 aat tac acg gta att ctg ggt cac tgt tac tac cat gga cat gta cgg       684
Asn Tyr Thr Val Ile Leu Gly His Cys Tyr Tyr His Gly His Val Arg
                115                 120                 125 gga tat tct gat tca gca gtc agt ctc agc acg tgt tct ggt ctc agg       732
Gly Tyr Ser Asp Ser Ala Val Ser Leu Ser Thr Cys Ser Gly Leu Arg
            130                 135                 140
```

| | |
|---|---:|
| gga ctt att gtg ttt gaa aat gaa agc tat gtc tta gaa cca atg aaa<br>Gly Leu Ile Val Phe Glu Asn Glu Ser Tyr Val Leu Glu Pro Met Lys<br>           145                   150                 155 | 780 |
| agt gca acc aac aga tac aaa ctc ttc cca gcg aag aag ctg aaa agc<br>Ser Ala Thr Asn Arg Tyr Lys Leu Phe Pro Ala Lys Lys Leu Lys Ser<br>    160                   165                 170 | 828 |
| gtc cgg gga tca tgt gga tca cat cac aac aca cca aac ctc gct gca<br>Val Arg Gly Ser Cys Gly Ser His His Asn Thr Pro Asn Leu Ala Ala<br>175                 180                 185               190 | 876 |
| aag aat gtg ttt cca cca ccc tct cag aca tgg gca aga agg cat aaa<br>Lys Asn Val Phe Pro Pro Pro Ser Gln Thr Trp Ala Arg Arg His Lys<br>           195                   200                 205 | 924 |
| aga gag acc ctc aag gca act aag tat gtg gag ctg gtg atc gtg gca<br>Arg Glu Thr Leu Lys Ala Thr Lys Tyr Val Glu Leu Val Ile Val Ala<br>           210                   215                 220 | 972 |
| gac aac cga gag ttt cag agg caa gga aaa gat ctg gaa aaa gtt aag<br>Asp Asn Arg Glu Phe Gln Arg Gln Gly Lys Asp Leu Glu Lys Val Lys<br>           225                   230                 235 | 1020 |
| cag cga tta ata gag att gct aat cac gtt gac aag ttt tac aga cca<br>Gln Arg Leu Ile Glu Ile Ala Asn His Val Asp Lys Phe Tyr Arg Pro<br>240                 245                 250 | 1068 |
| ctg aac att cgg atc gtg ttg gta ggc gtg gaa gtg tgg aat gac atg<br>Leu Asn Ile Arg Ile Val Leu Val Gly Val Glu Val Trp Asn Asp Met<br>255                 260                 265               270 | 1116 |
| gac aaa tgc tct gta agt cag gac cca ttc acc agc ctc cat gaa ttt<br>Asp Lys Cys Ser Val Ser Gln Asp Pro Phe Thr Ser Leu His Glu Phe<br>               275                 280               285 | 1164 |
| ctg gac tgg agg aag atg aag ctt cta cct cgc aaa tcc cat gac aat<br>Leu Asp Trp Arg Lys Met Lys Leu Leu Pro Arg Lys Ser His Asp Asn<br>           290                   295                 300 | 1212 |
| gcg cag ctt gtc agt ggg gtt tat ttc caa ggg acc acc atc ggc atg<br>Ala Gln Leu Val Ser Gly Val Tyr Phe Gln Gly Thr Thr Ile Gly Met<br>               305                 310               315 | 1260 |
| gcc cca atc atg agc atg tgc acg gca gac cag tct ggg gga att gtc<br>Ala Pro Ile Met Ser Met Cys Thr Ala Asp Gln Ser Gly Gly Ile Val<br>320                 325                 330 | 1308 |
| atg gac cat tca gac aat ccc ctt ggt gca gcc gtg acc ctg gca cat<br>Met Asp His Ser Asp Asn Pro Leu Gly Ala Ala Val Thr Leu Ala His<br>335                 340                 345               350 | 1356 |
| gag ctg ggc cac aat ttc ggg atg aat cat gac aca ctg gac agg ggc<br>Glu Leu Gly His Asn Phe Gly Met Asn His Asp Thr Leu Asp Arg Gly<br>               355                 360               365 | 1404 |
| tgt agc tgt caa atg gcg gtt gag aaa gga ggc tgc atc atg aac gct<br>Cys Ser Cys Gln Met Ala Val Glu Lys Gly Gly Cys Ile Met Asn Ala<br>           370                   375                 380 | 1452 |
| tcc acc ggg tac cca ttt ccc atg gtg ttc agc agt tgc agc agg aag<br>Ser Thr Gly Tyr Pro Phe Pro Met Val Phe Ser Ser Cys Ser Arg Lys<br>385                 390                 395 | 1500 |
| gac ttg gag acc agc ctg gag aaa gga atg ggg gtg tgc ctg ttt aac<br>Asp Leu Glu Thr Ser Leu Glu Lys Gly Met Gly Val Cys Leu Phe Asn<br>           400                   405               410 | 1548 |
| ctg ccg gaa gtc agg gag tct ttc ggg ggc cag aag tgt ggg aac aga<br>Leu Pro Glu Val Arg Glu Ser Phe Gly Gly Gln Lys Cys Gly Asn Arg<br>415                 420                 425               430 | 1596 |
| ttt gtg gaa gaa gga gag gag tgt gac tgt ggg gag cca gag gaa tgt<br>Phe Val Glu Glu Gly Glu Glu Cys Asp Cys Gly Glu Pro Glu Glu Cys<br>               435                 440               445 | 1644 |
| atg aat cgc tgc tgc aat gcc acc acc tgt acc ctg aag ccg gac gct<br>Met Asn Arg Cys Cys Asn Ala Thr Thr Cys Thr Leu Lys Pro Asp Ala | 1692 |

-continued

```
                450                 455                 460
gtg tgc gca cat ggg ctg tgc tgt gaa gac tgc cag ctg aag cct gca      1740
Val Cys Ala His Gly Leu Cys Cys Glu Asp Cys Gln Leu Lys Pro Ala
        465                 470                 475 gga aca gcg tgc agg gac tcc agc aac tcc tgt gac ctc cca gag ttc      1788
Gly Thr Ala Cys Arg Asp Ser Ser Asn Ser Cys Asp Leu Pro Glu Phe
480                 485                 490 tgc aca ggg gcc agc cct cac tgc cca gcc aac gtg tac ctg cac gat      1836
Cys Thr Gly Ala Ser Pro His Cys Pro Ala Asn Val Tyr Leu His Asp
495                 500                 505                 510 ggg cac tca tgt cag gat gtg gac ggc tac tgc tac aat ggc atc tgc      1884
Gly His Ser Cys Gln Asp Val Asp Gly Tyr Cys Tyr Asn Gly Ile Cys
                515                 520                 525 cag act cac gag cag cag tgt gtc aca ctc tgg gga cca ggt gct aaa      1932
Gln Thr His Glu Gln Gln Cys Val Thr Leu Trp Gly Pro Gly Ala Lys
                530                 535                 540 cct gcc cct ggg atc tgc ttt gag aga gtc aat tct gca ggt gat cct      1980
Pro Ala Pro Gly Ile Cys Phe Glu Arg Val Asn Ser Ala Gly Asp Pro
                545                 550                 555 tat ggc aac tgt ggc aaa gtc tcg aag agt tcc ttt gcc aaa tgc gag      2028
Tyr Gly Asn Cys Gly Lys Val Ser Lys Ser Ser Phe Ala Lys Cys Glu
            560                 565                 570 atg aga gat gct aaa tgt gga aaa atc cag tgt caa gga ggt gcc agc      2076
Met Arg Asp Ala Lys Cys Gly Lys Ile Gln Cys Gln Gly Gly Ala Ser
575                 580                 585                 590 cgg cca gtc att ggt acc aat gcc gtt tcc ata gaa aca aac atc ccc      2124
Arg Pro Val Ile Gly Thr Asn Ala Val Ser Ile Glu Thr Asn Ile Pro
                595                 600                 605 ctg cag caa gga ggc cgg att ctg tgc cgg ggg acc cac gtg tac ttg      2172
Leu Gln Gln Gly Gly Arg Ile Leu Cys Arg Gly Thr His Val Tyr Leu
                610                 615                 620 ggc gat gac atg ccg gac cca ggg ctt gtg ctt gca ggc aca aag tgt      2220
Gly Asp Asp Met Pro Asp Pro Gly Leu Val Leu Ala Gly Thr Lys Cys
                625                 630                 635 gca gat gga aaa atc tgc ctg aat cgt caa tgt caa aat att agt gtc      2268
Ala Asp Gly Lys Ile Cys Leu Asn Arg Gln Cys Gln Asn Ile Ser Val
640                 645                 650 ttt ggg gtt cac gag tgt gca atg cag tgc cac ggc aga ggg gtg tgc      2316
Phe Gly Val His Glu Cys Ala Met Gln Cys His Gly Arg Gly Val Cys
655                 660                 665                 670 aac aac agg aag aac tgc cac tgc gag gcc cac tgg gca cct ccc ttc      2364
Asn Asn Arg Lys Asn Cys His Cys Glu Ala His Trp Ala Pro Pro Phe
                675                 680                 685 tgt gac aag ttt ggc ttt gga gga agc aca gac agc ggc ccc atc cgg      2412
Cys Asp Lys Phe Gly Phe Gly Gly Ser Thr Asp Ser Gly Pro Ile Arg
            690                 695                 700 caa gca gat aac caa ggt tta acc ata gga att ctg gtg acc atc ctg      2460
Gln Ala Asp Asn Gln Gly Leu Thr Ile Gly Ile Leu Val Thr Ile Leu
            705                 710                 715 tgt ctt ctt gct gcc gga ttt gtg gtt tat ctc aaa agg aag acc ttg      2508
Cys Leu Leu Ala Ala Gly Phe Val Val Tyr Leu Lys Arg Lys Thr Leu
        720                 725                 730 ata cga ctg ctg ttt aca aat aag aag acc acc att gaa aaa cta agg      2556
Ile Arg Leu Leu Phe Thr Asn Lys Lys Thr Thr Ile Glu Lys Leu Arg
735                 740                 745                 750 tgt gtg cgc cct tcc cgg cca ccc cgt ggc ttc caa ccc tgt cag gct      2604
Cys Val Arg Pro Ser Arg Pro Pro Arg Gly Phe Gln Pro Cys Gln Ala
                755                 760                 765 cac ctc ggc cac ctt gga aaa ggc ctg atg agg aag ccg cca gat tcc      2652
```

```
                His Leu Gly His Leu Gly Lys Gly Leu Met Arg Lys Pro Pro Asp Ser
                            770                 775                 780 tac cca ccg aag gac aat ccc agg aga ttg ctg cag tgt cag aat gtt           2700
Tyr Pro Pro Lys Asp Asn Pro Arg Arg Leu Leu Gln Cys Gln Asn Val
            785                 790                 795 gac atc agc aga ccc ctc aac ggc ctg aat gtc cct cag ccc cag tca           2748
Asp Ile Ser Arg Pro Leu Asn Gly Leu Asn Val Pro Gln Pro Gln Ser
        800                 805                 810 act cag cga gtg ctt cct ccc ctc cac cgg gcc cca cgt gca cct agc           2796
Thr Gln Arg Val Leu Pro Pro Leu His Arg Ala Pro Arg Ala Pro Ser
815                 820                 825                 830 gtc cct gcc aga ccc ctg cca gcc aag cct gca ctt agg cag gcc cag           2844
Val Pro Ala Arg Pro Leu Pro Ala Lys Pro Ala Leu Arg Gln Ala Gln
                835                 840                 845 ggg acc tgt aag cca aac ccc cct cag aag cct ctg cct gca gat cct           2892
Gly Thr Cys Lys Pro Asn Pro Pro Gln Lys Pro Leu Pro Ala Asp Pro
            850                 855                 860 ctg gcc aga aca act cgg ctc act cat gcc ttg gcc agg acc cca gga           2940
Leu Ala Arg Thr Thr Arg Leu Thr His Ala Leu Ala Arg Thr Pro Gly
        865                 870                 875 caa tgg gag act ggg ctc cgc ctg gca ccc ctc aga cct gct cca caa           2988
Gln Trp Glu Thr Gly Leu Arg Leu Ala Pro Leu Arg Pro Ala Pro Gln
    880                 885                 890 tat cca cac caa gtg ccc aga tcc acc cac acc gcc tat att aag tga           3036
Tyr Pro His Gln Val Pro Arg Ser Thr His Thr Ala Tyr Ile Lys
895                 900                 905 gaagccgaca cctttttca acagtgaaga cagaagtttg cactatcttt cagctccagt          3096
tggagttttt tgtaccaact tttaggattt ttttttaatgt ttaaaacatc attactataa       3156
gaactttgag ctactgccgt cagtgctgtg ctgtgctatg gtgctctgtc tacttgcaca        3216
ggtacttgta aattattaat ttatgcagaa tgttgattac agtgcagtgc gctgtagtag       3276 gcattttac catcactgag ttttccatgg caggaaggct tgttgtgctt ttagtatttt         3336
agtgaacttg aaatatcctg cttgatggga ttctggacag gatgtgtttg ctttctgatc       3396
aaggccttat tggaaagcag tcccccaact accccagct gtgcttatgg taccagatgc        3456
agctcaagag atcccaagta gaatctcagt tgattttctg gattccccat ctcaggccag      3516
agccaagggg cttcaggtcc aggctgtgtt tggctttcag ggaggccctg tgccccttga       3576
caactggcag gcaggctccc agggacacct gggagaaatc tggcttctgg ccaggaagct       3636
ttggtgagaa cctgggttgc agacaggaat cttaaggtgt agccacacca ggatagagac        3696
tggaacacta gacaagccag aacttgaccc tgagctgacc agccgtgagc atgtttggaa         3756
ggggtctgta gtgtcactca aggcggtgct tgatagaaat gccaagcact tcttttctc        3816 gctgtccttt ctagagcact gccaccagta ggttatttag cttgggaaag gtggtgtttc        3876
tgtaagaaac ctactgccca ggcactgcaa accgccacct ccctatactg cttggagctg         3936
agcaaatcac cacaaactgt aatacaatga tcctgtattc agacagatga ggactttcca       3996
tgggaccaca actattttca gatgtgaacc attaaccaga tctagtcaat caagtctgtt        4056
tactgcaagg ttcaacttat taacaattag gcagactctt tatgcttgca aaaactacaa       4116
ccaatggaat gtgatgttca tgggtatagt tcatgtctgc tatcattatt cgtagatatt       4176
ggacaaagaa ccttctctat ggggcatcct cttttccaa cttggctgca ggaatcttta       4236
aaagatgctt ttaacagagt ctgaacctat ttcttaaaca cttgcaacct acctgttgag       4296
catcacagaa tgtgataagg aaatcaactt gcttatcaac ttcctaaata ttatgagatg        4356
```

```
tggcttgggc agcatcccct tgaactcttc actcttcaaa tgcctgacta gggagccatg    4416
tttcacaagg tctttaaagt gactaatggc atgagaaata caaaaatact cagataaggt    4476
aaaatgccat gatgcctctg tcttctggac tggttttcac attagaagac aattgacaac    4536
agttacataa ttcactctga gtgttttatg agaaagcctt cttttggggt caacagtttt    4596
cctatgcttt gaaacagaaa aatatgtacc aagaatcttg gtttgccttc cagaaaacaa    4656
aactgcattt cactttcccg gtgttcccca ctgtatctag caacatagt attcatgact     4716 atggataaac taaacacgtg acacaaacac acacaaaagg gaacccagct ctaatacatt    4776
ccaactcgta tagcatgcat ctgttttattc tatagttatt aagttcttta aaatgtaaag   4836
ccatgctgga aaataatact gctgagatac atacagaatt actgtaactg attcacttg    4896 gtaattgtac taaagccaaa catatatata ctattaaaaa ggtttacaga attttatggt    4956
gcattacgtg ggcattgtct ttttagatgc ccaaatcctt agatctggca tgttagccct    5016
tcctccaatt ataagaggat atgaaccaaa aaaaaaaaaa aaaaaa                   5062
```

<210> SEQ ID NO 2
<211> LENGTH: 909
<212> TYPE: PRT
<213> ORGANISM: Homo sapiens

<400> SEQUENCE: 2

```
Met Ala Ala Arg Pro Leu Pro Val Ser Pro Ala Arg Ala Leu Leu Leu
1               5                   10                  15

Ala Leu Ala Gly Ala Leu Leu Ala Pro Cys Glu Ala Arg Gly Val Ser
            20                  25                  30

Leu Trp Asn Gln Gly Arg Ala Asp Glu Val Val Ser Ala Ser Val Arg
        35                  40                  45

Ser Gly Asp Leu Trp Ile Pro Val Lys Ser Phe Asp Ser Lys Asn His
    50                  55                  60

Pro Glu Val Leu Asn Ile Arg Leu Gln Arg Glu Ser Lys Glu Leu Ile
65                  70                  75                  80

Ile Asn Leu Glu Arg Asn Glu Gly Leu Ile Ala Ser Ser Phe Thr Glu
                85                  90                  95

Thr His Tyr Leu Gln Asp Gly Thr Asp Val Ser Leu Ala Arg Asn Tyr
            100                 105                 110

Thr Val Ile Leu Gly His Cys Tyr Tyr His Gly His Val Arg Gly Tyr
        115                 120                 125

Ser Asp Ser Ala Val Ser Leu Ser Thr Cys Ser Gly Leu Arg Gly Leu
    130                 135                 140

Ile Val Phe Glu Asn Glu Ser Tyr Val Leu Glu Pro Met Lys Ser Ala
145                 150                 155                 160

Thr Asn Arg Tyr Lys Leu Phe Pro Ala Lys Lys Leu Lys Ser Val Arg
                165                 170                 175

Gly Ser Cys Gly Ser His His Asn Thr Pro Asn Leu Ala Ala Lys Asn
            180                 185                 190

Val Phe Pro Pro Ser Gln Thr Trp Ala Arg His Lys Arg Glu
        195                 200                 205

Thr Leu Lys Ala Thr Lys Tyr Val Glu Leu Val Ile Val Ala Asp Asn
    210                 215                 220

Arg Glu Phe Gln Arg Gln Gly Lys Asp Leu Glu Lys Val Lys Gln Arg
225                 230                 235                 240

Leu Ile Glu Ile Ala Asn His Val Asp Lys Phe Tyr Arg Pro Leu Asn
                245                 250                 255
```

-continued

```
Ile Arg Ile Val Leu Val Gly Val Glu Val Trp Asn Asp Met Asp Lys
            260                 265                 270
Cys Ser Val Ser Gln Asp Pro Phe Thr Ser Leu His Glu Phe Leu Asp
        275                 280                 285
Trp Arg Lys Met Lys Leu Leu Pro Arg Lys Ser His Asp Asn Ala Gln
290                 295                 300
Leu Val Ser Gly Val Tyr Phe Gln Gly Thr Thr Ile Gly Met Ala Pro
305                 310                 315                 320
Ile Met Ser Met Cys Thr Ala Asp Gln Ser Gly Gly Ile Val Met Asp
                325                 330                 335
His Ser Asp Asn Pro Leu Gly Ala Ala Val Thr Leu Ala His Glu Leu
            340                 345                 350
Gly His Asn Phe Gly Met Asn His Asp Thr Leu Asp Arg Gly Cys Ser
        355                 360                 365
Cys Gln Met Ala Val Glu Lys Gly Gly Cys Ile Met Asn Ala Ser Thr
    370                 375                 380
Gly Tyr Pro Phe Pro Met Val Phe Ser Ser Cys Ser Arg Lys Asp Leu
385                 390                 395                 400
Glu Thr Ser Leu Glu Lys Gly Met Gly Val Cys Leu Phe Asn Leu Pro
                405                 410                 415
Glu Val Arg Glu Ser Phe Gly Gly Gln Lys Cys Gly Asn Arg Phe Val
            420                 425                 430
Glu Glu Gly Glu Glu Cys Asp Cys Gly Glu Pro Glu Glu Cys Met Asn
        435                 440                 445
Arg Cys Cys Asn Ala Thr Thr Cys Thr Leu Lys Pro Asp Ala Val Cys
    450                 455                 460
Ala His Gly Leu Cys Cys Glu Asp Cys Gln Leu Lys Pro Ala Gly Thr
465                 470                 475                 480
Ala Cys Arg Asp Ser Ser Asn Ser Cys Asp Leu Pro Glu Phe Cys Thr
                485                 490                 495
Gly Ala Ser Pro His Cys Pro Ala Asn Val Tyr Leu His Asp Gly His
            500                 505                 510
Ser Cys Gln Asp Val Asp Gly Tyr Cys Tyr Asn Gly Ile Cys Gln Thr
        515                 520                 525
His Glu Gln Gln Cys Val Thr Leu Trp Gly Pro Gly Ala Lys Pro Ala
    530                 535                 540
Pro Gly Ile Cys Phe Glu Arg Val Asn Ser Ala Gly Asp Pro Tyr Gly
545                 550                 555                 560
Asn Cys Gly Lys Val Ser Lys Ser Ser Phe Ala Lys Cys Glu Met Arg
                565                 570                 575
Asp Ala Lys Cys Gly Lys Ile Gln Cys Gln Gly Gly Ala Ser Arg Pro
            580                 585                 590
Val Ile Gly Thr Asn Ala Val Ser Ile Glu Thr Asn Ile Pro Leu Gln
        595                 600                 605
Gln Gly Gly Arg Ile Leu Cys Arg Gly Thr His Val Tyr Leu Gly Asp
    610                 615                 620
Asp Met Pro Asp Pro Gly Leu Val Leu Ala Gly Thr Lys Cys Ala Asp
625                 630                 635                 640
Gly Lys Ile Cys Leu Asn Arg Gln Cys Gln Asn Ile Ser Val Phe Gly
                645                 650                 655
Val His Glu Cys Ala Met Gln Cys His Gly Arg Gly Val Cys Asn Asn
            660                 665                 670
```

```
Arg Lys Asn Cys His Cys Glu Ala His Trp Ala Pro Pro Phe Cys Asp
        675                 680                 685

Lys Phe Gly Phe Gly Ser Thr Asp Ser Gly Pro Ile Arg Gln Ala
    690                 695                 700

Asp Asn Gln Gly Leu Thr Ile Gly Ile Leu Val Thr Ile Leu Cys Leu
705                 710                 715                 720

Leu Ala Ala Gly Phe Val Val Tyr Leu Lys Arg Lys Thr Leu Ile Arg
                725                 730                 735

Leu Leu Phe Thr Asn Lys Lys Thr Thr Ile Glu Lys Leu Arg Cys Val
            740                 745                 750

Arg Pro Ser Arg Pro Pro Arg Gly Phe Gln Pro Cys Gln Ala His Leu
        755                 760                 765

Gly His Leu Gly Lys Gly Leu Met Arg Lys Pro Asp Ser Tyr Pro
    770                 775                 780

Pro Lys Asp Asn Pro Arg Arg Leu Leu Gln Cys Gln Asn Val Asp Ile
785                 790                 795                 800

Ser Arg Pro Leu Asn Gly Leu Asn Val Pro Gln Pro Ser Thr Gln
                805                 810                 815

Arg Val Leu Pro Pro Leu His Arg Ala Pro Arg Ala Pro Ser Val Pro
            820                 825                 830

Ala Arg Pro Leu Pro Ala Lys Pro Ala Leu Arg Gln Ala Gln Gly Thr
        835                 840                 845

Cys Lys Pro Asn Pro Pro Gln Lys Pro Leu Pro Ala Asp Pro Leu Ala
850                 855                 860

Arg Thr Thr Arg Leu Thr His Ala Leu Ala Arg Thr Pro Gly Gln Trp
865                 870                 875                 880

Glu Thr Gly Leu Arg Leu Ala Pro Leu Arg Pro Ala Pro Gln Tyr Pro
                885                 890                 895

His Gln Val Pro Arg Ser Thr His Thr Ala Tyr Ile Lys
                900                 905

<210> SEQ ID NO 3
<211> LENGTH: 3328
<212> TYPE: DNA
<213> ORGANISM: Homo sapiens
<220> FEATURE:
<221> NAME/KEY: CDS
<222> LOCATION: (307)..(2523)
<223> OTHER INFORMATION:

<400> SEQUENCE: 3
cactaacgct cttcctagtc cccgggccaa ctcggacagt ttgctcattt attgcaacgg      60
tcaaggctgg cttgtgccag aacggcgcgc gcgcgacgca cgcacacaca cgggggaaa     120 cttttttaaa aatgaaaggc tagaagagct cagcggcggc gcgggccgtg cgcgagggct    180
ccggagctga ctcgccgagg caggaaatcc ctccggtcgc gacgcccggc cccgctcggc    240
gcccgcgtgg gatggtgcag cgctcgccgc cgggcccgag agctgctgca ctgaaggccg    300 gcgacg atg gca gcg cgc ccg ctg ccc gtg tcc ccc gcc cgc gcc ctc       348
       Met Ala Ala Arg Pro Leu Pro Val Ser Pro Ala Arg Ala Leu
         1               5                  10 ctg ctc gcc ctg gcc ggt gct ctg ctc gcg ccc tgc gag gcc cga ggg      396
Leu Leu Ala Leu Ala Gly Ala Leu Leu Ala Pro Cys Glu Ala Arg Gly
15                  20                  25                  30 gtg agc tta tgg aac gaa gga aga gct gat gaa gtt gtc agt gcc tct      444
Val Ser Leu Trp Asn Glu Gly Arg Ala Asp Glu Val Val Ser Ala Ser
                35                  40                  45
```

-continued

| | |
|---|---|
| gtt cgg agt ggg gac ctc tgg atc cca gtg aag agc ttc gac tcc aag<br>Val Arg Ser Gly Asp Leu Trp Ile Pro Val Lys Ser Phe Asp Ser Lys<br>          50                      55                      60 | 492 |
| aat cat cca gaa gtg ctg aat att cga cta caa cgg gaa agc aaa gaa<br>Asn His Pro Glu Val Leu Asn Ile Arg Leu Gln Arg Glu Ser Lys Glu<br>        65                      70                      75 | 540 |
| ctg atc ata aat ctg gaa aga aat gaa ggt ctc att gcc agc agt ttc<br>Leu Ile Ile Asn Leu Glu Arg Asn Glu Gly Leu Ile Ala Ser Ser Phe<br>80                      85                      90 | 588 |
| acg gaa acc cac tat ctg caa gac ggt act gat gtc tcc ctc gct cga<br>Thr Glu Thr His Tyr Leu Gln Asp Gly Thr Asp Val Ser Leu Ala Arg<br>95                      100                    105              110 | 636 |
| aat tac acg gta att ctg ggt cac tgt tac tac cat gga cat gta cgg<br>Asn Tyr Thr Val Ile Leu Gly His Cys Tyr Tyr His Gly His Val Arg<br>                    115                    120                    125 | 684 |
| gga tat tct gat tca gca gtc agt ctc agc acg tgt tct ggt ctc agg<br>Gly Tyr Ser Asp Ser Ala Val Ser Leu Ser Thr Cys Ser Gly Leu Arg<br>                    130                    135                    140 | 732 |
| gga ctt att gtg ttt gaa aat gaa agc tat gtc tta gaa cca atg aaa<br>Gly Leu Ile Val Phe Glu Asn Glu Ser Tyr Val Leu Glu Pro Met Lys<br>                    145                    150                    155 | 780 |
| agt gca acc aac aga tac aaa ctc ttc cca gcg aag aag ctg aaa agc<br>Ser Ala Thr Asn Arg Tyr Lys Leu Phe Pro Ala Lys Lys Leu Lys Ser<br>      160                    165                    170 | 828 |
| gtc cgg gga tca tgt gga tca cat cac aac aca cca aac ctc gct gca<br>Val Arg Gly Ser Cys Gly Ser His His Asn Thr Pro Asn Leu Ala Ala<br>175                      180                    185                    190 | 876 |
| aag aat gtg ttt cca cca ccc tct cag aca tgg gca aga agg cat aaa<br>Lys Asn Val Phe Pro Pro Pro Ser Gln Thr Trp Ala Arg Arg His Lys<br>                    195                    200                    205 | 924 |
| aga gag acc ctc aag gca act aag tat gtg gag ctg gtg atc gtg gca<br>Arg Glu Thr Leu Lys Ala Thr Lys Tyr Val Glu Leu Val Ile Val Ala<br>                    210                    215                    220 | 972 |
| gac aac cga gag ttt cag agg caa gga aaa gat ctg gaa aaa gtt aag<br>Asp Asn Arg Glu Phe Gln Arg Gln Gly Lys Asp Leu Glu Lys Val Lys<br>              225                    230                    235 | 1020 |
| cag cga tta ata gag att gct aat cac gtt gac aag ttt tac aga cca<br>Gln Arg Leu Ile Glu Ile Ala Asn His Val Asp Lys Phe Tyr Arg Pro<br>240                      245                    250 | 1068 |
| ctg aac att cgg atc gtg ttg gta ggc gtg gaa gtg tgg aat gac atg<br>Leu Asn Ile Arg Ile Val Leu Val Gly Val Glu Val Trp Asn Asp Met<br>255                      260                    265                    270 | 1116 |
| gac aaa tgc tct gta agt cag gac cca ttc acc agc ctc cat gaa ttt<br>Asp Lys Cys Ser Val Ser Gln Asp Pro Phe Thr Ser Leu His Glu Phe<br>                    275                    280                    285 | 1164 |
| ctg gac tgg agg aag atg aag ctt cta cct cgc aaa tcc cat gac aat<br>Leu Asp Trp Arg Lys Met Lys Leu Leu Pro Arg Lys Ser His Asp Asn<br>                    290                    295                    300 | 1212 |
| gcg cag ctt gtc agt ggg gtt tat ttc caa ggg acc acc atc ggc atg<br>Ala Gln Leu Val Ser Gly Val Tyr Phe Gln Gly Thr Thr Ile Gly Met<br>              305                    310                    315 | 1260 |
| gcc cca atc atg agc atg tgc acg gca gac cag tct ggg gga att gtc<br>Ala Pro Ile Met Ser Met Cys Thr Ala Asp Gln Ser Gly Gly Ile Val<br>320                      325                    330 | 1308 |
| atg gac cat tca gac aat ccc ctt ggt gca gcc gtg acc ctg gca cat<br>Met Asp His Ser Asp Asn Pro Leu Gly Ala Ala Val Thr Leu Ala His<br>335                      340                    345              350 | 1356 |
| gag ctg ggc cac aat ttc ggg atg aat cat gac aca ctg gac agg ggc<br>Glu Leu Gly His Asn Phe Gly Met Asn His Asp Thr Leu Asp Arg Gly<br>                    355                    360                    365 | 1404 |

-continued

| | | | | | | | | | | | | | | |
|---|---|---|---|---|---|---|---|---|---|---|---|---|---|---|
| tgt | agc | tgt | caa | atg | gcg | gtt | gag | aaa | gga | ggc | tgc | atc | atg | aac gct | 1452 |
| Cys | Ser | Cys | Gln | Met | Ala | Val | Glu | Lys | Gly | Gly | Cys | Ile | Met | Asn Ala | |
| | | 370 | | | | | 375 | | | | | 380 | | | |

| tcc | acc | ggg | tac | cca | ttt | ccc | atg | gtg | ttc | agc | agt | tgc | agc | agg aag | 1500 |
| Ser | Thr | Gly | Tyr | Pro | Phe | Pro | Met | Val | Phe | Ser | Ser | Cys | Ser | Arg Lys | |
| | 385 | | | | | 390 | | | | | 395 | | | | |

| gac | ttg | gag | acc | agc | ctg | gag | aaa | gga | atg | ggg | gtg | tgc | ctg | ttt aac | 1548 |
| Asp | Leu | Glu | Thr | Ser | Leu | Glu | Lys | Gly | Met | Gly | Val | Cys | Leu | Phe Asn | |
| 400 | | | | | 405 | | | | | 410 | | | | | |

| ctg | ccg | gaa | gtc | agg | gag | tct | ttc | ggg | ggc | cag | aag | tgt | ggg | aac aga | 1596 |
| Leu | Pro | Glu | Val | Arg | Glu | Ser | Phe | Gly | Gly | Gln | Lys | Cys | Gly | Asn Arg | |
| 415 | | | | | 420 | | | | | 425 | | | | | 430 |

| ttt | gtg | gaa | gaa | gga | gag | gag | tgt | gac | tgt | ggg | gag | cca | gag | gaa tgt | 1644 |
| Phe | Val | Glu | Glu | Gly | Glu | Glu | Cys | Asp | Cys | Gly | Glu | Pro | Glu | Glu Cys | |
| | | | | 435 | | | | | 440 | | | | | 445 | |

| atg | aat | cgc | tgc | tgc | aat | gcc | acc | acc | tgt | acc | ctg | aag | ccg | gac gct | 1692 |
| Met | Asn | Arg | Cys | Cys | Asn | Ala | Thr | Thr | Cys | Thr | Leu | Lys | Pro | Asp Ala | |
| | | | 450 | | | | | 455 | | | | | 460 | | |

| gtg | tgc | gca | cat | ggg | ctg | tgc | tgt | gaa | gac | tgc | cag | ctg | aag | cct gca | 1740 |
| Val | Cys | Ala | His | Gly | Leu | Cys | Cys | Glu | Asp | Cys | Gln | Leu | Lys | Pro Ala | |
| | | 465 | | | | | 470 | | | | | 475 | | | |

| gga | aca | gcg | tgc | agg | gac | tcc | agc | aac | tcc | tgt | gac | ctc | cca | gag ttc | 1788 |
| Gly | Thr | Ala | Cys | Arg | Asp | Ser | Ser | Asn | Ser | Cys | Asp | Leu | Pro | Glu Phe | |
| 480 | | | | | 485 | | | | | 490 | | | | | |

| tgc | aca | ggg | gcc | agc | cct | cac | tgc | cca | gcc | aac | gtg | tac | ctg | cac gat | 1836 |
| Cys | Thr | Gly | Ala | Ser | Pro | His | Cys | Pro | Ala | Asn | Val | Tyr | Leu | His Asp | |
| 495 | | | | | 500 | | | | | 505 | | | | | 510 |

| ggg | cac | tca | tgt | cag | gat | gtg | gac | ggc | tac | tgc | tac | aat | ggc | atc tgc | 1884 |
| Gly | His | Ser | Cys | Gln | Asp | Val | Asp | Gly | Tyr | Cys | Tyr | Asn | Gly | Ile Cys | |
| | | | | 515 | | | | | 520 | | | | | 525 | |

| cag | act | cac | gag | cag | cag | tgt | gtc | aca | ctc | tgg | gga | cca | ggt | gct aaa | 1932 |
| Gln | Thr | His | Glu | Gln | Gln | Cys | Val | Thr | Leu | Trp | Gly | Pro | Gly | Ala Lys | |
| | | | 530 | | | | | 535 | | | | | 540 | | |

| cct | gcc | cct | ggg | atc | tgc | ttt | gag | aga | gtc | aat | tct | gca | ggt | gat cct | 1980 |
| Pro | Ala | Pro | Gly | Ile | Cys | Phe | Glu | Arg | Val | Asn | Ser | Ala | Gly | Asp Pro | |
| | | 545 | | | | | 550 | | | | | 555 | | | |

| tat | ggc | aac | tgt | ggc | aaa | gtc | tcg | aag | agt | tcc | ttt | gcc | aaa | tgc gag | 2028 |
| Tyr | Gly | Asn | Cys | Gly | Lys | Val | Ser | Lys | Ser | Ser | Phe | Ala | Lys | Cys Glu | |
| | 560 | | | | | 565 | | | | | 570 | | | | |

| atg | aga | gat | gct | aaa | tgt | gga | aaa | atc | cag | tgt | caa | gga | ggt | gcc agc | 2076 |
| Met | Arg | Asp | Ala | Lys | Cys | Gly | Lys | Ile | Gln | Cys | Gln | Gly | Gly | Ala Ser | |
| 575 | | | | | 580 | | | | | 585 | | | | | 590 |

| cgg | cca | gtc | att | ggt | acc | aat | gcc | gtt | tcc | ata | gaa | aca | aac | atc ccc | 2124 |
| Arg | Pro | Val | Ile | Gly | Thr | Asn | Ala | Val | Ser | Ile | Glu | Thr | Asn | Ile Pro | |
| | | | | 595 | | | | | 600 | | | | | 605 | |

| ctg | cag | caa | gga | ggc | cgg | att | ctg | tgc | cgg | ggg | acc | cac | gtg | tac ttg | 2172 |
| Leu | Gln | Gln | Gly | Gly | Arg | Ile | Leu | Cys | Arg | Gly | Thr | His | Val | Tyr Leu | |
| | | | | 610 | | | | | 615 | | | | | 620 | |

| ggc | gat | gac | atg | ccg | gac | cca | ggg | ctt | gtg | ctt | gca | ggc | aca | aag tgt | 2220 |
| Gly | Asp | Asp | Met | Pro | Asp | Pro | Gly | Leu | Val | Leu | Ala | Gly | Thr | Lys Cys | |
| | | 625 | | | | | 630 | | | | | 635 | | | |

| gca | gat | gga | aaa | atc | tgc | ctg | aat | cgt | caa | tgt | caa | aat | att | agt gtc | 2268 |
| Ala | Asp | Gly | Lys | Ile | Cys | Leu | Asn | Arg | Gln | Cys | Gln | Asn | Ile | Ser Val | |
| | 640 | | | | | 645 | | | | | 650 | | | | |

| ttt | ggg | gtt | cac | gag | tgt | gca | atg | cag | tgc | cac | ggc | aga | ggg | gtg tgc | 2316 |
| Phe | Gly | Val | His | Glu | Cys | Ala | Met | Gln | Cys | His | Gly | Arg | Gly | Val Cys | |
| 655 | | | | | 660 | | | | | 665 | | | | | 670 |

| aac | aac | agg | aag | aac | tgc | cac | tgc | gag | gcc | cac | tgg | gca | cct | ccc ttc | 2364 |
| Asn | Asn | Arg | Lys | Asn | Cys | His | Cys | Glu | Ala | His | Trp | Ala | Pro | Pro Phe | |

```
                675                 680                 685
tgt gac aag ttt ggc ttt gga gga agc aca gac agc ggc ccc atc cgg      2412
Cys Asp Lys Phe Gly Phe Gly Gly Ser Thr Asp Ser Gly Pro Ile Arg
            690                 695                 700 caa gca gaa gca agg cag gaa gct gca gag tcc aac agg gag cgc ggc      2460
Gln Ala Glu Ala Arg Gln Glu Ala Ala Glu Ser Asn Arg Glu Arg Gly
        705                 710                 715 cag ggc cag gag ccc gtg gga tcg cag gag cat gcg tct act gcc tca     2508
Gln Gly Gln Glu Pro Val Gly Ser Gln Glu His Ala Ser Thr Ala Ser
    720                 725                 730 ctg aca ctc atc tga gccctcccat gacatggaga ccgtgaccag tgctgctgca     2563
Leu Thr Leu Ile
735 gaggaggtca cgcgtcccca aggcctcctg tgactggcag cattgactct gtggctttgc   2623
catcgtttcc atgacaacag acacaacaca gttctcgggg ctcaggaggg gaagtccagc   2683
ctaccaggca ggtctgcaga aacagtgcaa ggaagggca cgacttcctg gttgagcttc    2743
tgctaaaaca tggacatgct tcagtgctgc tcctgagaga gtagcaggtt accactctgg   2803
caggccccag ccctgcagca aggaggaaga ggactcaaaa gtctggcctt tcactgagcc   2863
tccacagcag tgggggagaa gcaagggttg ggcccagtgt cccctttccc cagtgacacc   2923
tccgccttgg cagccctgat gactggtctc tggctgcaac ttaatgctct gatatggctt   2983
ttagcattta ttatatgaaa atagcagggt tttagttttt aatttatcag agaccctgcc   3043
acccattcca tctccatcca agcaaactga atggcattga acaaactgg agaagaaggt    3103
aggagaaagg gcggtgaact ctggctcttt gctgtggaca tgcgtgacca gcagtactca   3163
ggtttgaggg tttgcagaaa gccagggaac ccacagagtc accaacccctt catttaacaa  3223
gtaagaatgt taaaaagtga aaacaatgta agagcctaac tccatccccc gtggccatta   3283
ctgcataaaa atagagtgca ttttgaaata aaaaaaaaaa aaaaa                   3328

<210> SEQ ID NO 4
<211> LENGTH: 738
<212> TYPE: PRT
<213> ORGANISM: Homo sapiens

<400> SEQUENCE: 4

Met Ala Ala Arg Pro Leu Pro Val Ser Pro Ala Arg Ala Leu Leu Leu
1               5                   10                  15

Ala Leu Ala Gly Ala Leu Leu Ala Pro Cys Glu Ala Arg Gly Val Ser
            20                  25                  30

Leu Trp Asn Glu Gly Arg Ala Asp Glu Val Val Ser Ala Ser Val Arg
        35                  40                  45

Ser Gly Asp Leu Trp Ile Pro Val Lys Ser Phe Asp Ser Lys Asn His
    50                  55                  60

Pro Glu Val Leu Asn Ile Arg Leu Gln Arg Glu Ser Lys Glu Leu Ile
65                  70                  75                  80

Ile Asn Leu Glu Arg Asn Glu Gly Leu Ile Ala Ser Ser Phe Thr Glu
                85                  90                  95

Thr His Tyr Leu Gln Asp Gly Thr Asp Val Ser Leu Ala Arg Asn Tyr
            100                 105                 110

Thr Val Ile Leu Gly His Cys Tyr Tyr His Gly His Val Arg Gly Tyr
        115                 120                 125

Ser Asp Ser Ala Val Ser Leu Ser Thr Cys Ser Gly Leu Arg Gly Leu
    130                 135                 140
```

```
Ile Val Phe Glu Asn Glu Ser Tyr Val Leu Glu Pro Met Lys Ser Ala
145                 150                 155                 160

Thr Asn Arg Tyr Lys Leu Phe Pro Ala Lys Lys Leu Lys Ser Val Arg
                165                 170                 175

Gly Ser Cys Gly Ser His His Asn Thr Pro Asn Leu Ala Ala Lys Asn
            180                 185                 190

Val Phe Pro Pro Ser Gln Thr Trp Ala Arg Arg His Lys Arg Glu
                195                 200                 205

Thr Leu Lys Ala Thr Lys Tyr Val Glu Leu Val Ile Val Ala Asp Asn
    210                 215                 220

Arg Glu Phe Gln Arg Gln Gly Lys Asp Leu Glu Lys Val Lys Gln Arg
225                 230                 235                 240

Leu Ile Glu Ile Ala Asn His Val Asp Lys Phe Tyr Arg Pro Leu Asn
                245                 250                 255

Ile Arg Ile Val Leu Val Gly Val Glu Val Trp Asn Asp Met Asp Lys
                260                 265                 270

Cys Ser Val Ser Gln Asp Pro Phe Thr Ser Leu His Glu Phe Leu Asp
                275                 280                 285

Trp Arg Lys Met Lys Leu Leu Pro Arg Lys Ser His Asp Asn Ala Gln
290                 295                 300

Leu Val Ser Gly Val Tyr Phe Gln Gly Thr Thr Ile Gly Met Ala Pro
305                 310                 315                 320

Ile Met Ser Met Cys Thr Ala Asp Gln Ser Gly Gly Ile Val Met Asp
                325                 330                 335

His Ser Asp Asn Pro Leu Gly Ala Ala Val Thr Leu Ala His Glu Leu
                340                 345                 350

Gly His Asn Phe Gly Met Asn His Asp Thr Leu Asp Arg Gly Cys Ser
                355                 360                 365

Cys Gln Met Ala Val Glu Lys Gly Gly Cys Ile Met Asn Ala Ser Thr
            370                 375                 380

Gly Tyr Pro Phe Pro Met Val Phe Ser Ser Cys Ser Arg Lys Asp Leu
385                 390                 395                 400

Glu Thr Ser Leu Glu Lys Gly Met Gly Val Cys Leu Phe Asn Leu Pro
                405                 410                 415

Glu Val Arg Glu Ser Phe Gly Gly Gln Lys Cys Gly Asn Arg Phe Val
                420                 425                 430

Glu Glu Gly Glu Glu Cys Asp Cys Gly Glu Pro Glu Glu Cys Met Asn
            435                 440                 445

Arg Cys Cys Asn Ala Thr Thr Cys Thr Leu Lys Pro Asp Ala Val Cys
    450                 455                 460

Ala His Gly Leu Cys Cys Glu Asp Cys Gln Leu Lys Pro Ala Gly Thr
465                 470                 475                 480

Ala Cys Arg Asp Ser Ser Asn Ser Cys Asp Leu Pro Glu Phe Cys Thr
                485                 490                 495

Gly Ala Ser Pro His Cys Pro Ala Asn Val Tyr Leu His Asp Gly His
                500                 505                 510

Ser Cys Gln Asp Val Asp Gly Tyr Cys Tyr Asn Gly Ile Cys Gln Thr
            515                 520                 525

His Glu Gln Gln Cys Val Thr Leu Trp Gly Pro Gly Ala Lys Pro Ala
    530                 535                 540

Pro Gly Ile Cys Phe Glu Arg Val Asn Ser Ala Gly Asp Pro Tyr Gly
545                 550                 555                 560

Asn Cys Gly Lys Val Ser Lys Ser Ser Phe Ala Lys Cys Glu Met Arg
```

```
                    565                 570                 575
Asp Ala Lys Cys Gly Lys Ile Gln Cys Gln Gly Gly Ala Ser Arg Pro
            580                 585                 590
Val Ile Gly Thr Asn Ala Val Ser Ile Glu Thr Asn Ile Pro Leu Gln
            595                 600                 605
Gln Gly Gly Arg Ile Leu Cys Arg Gly Thr His Val Tyr Leu Gly Asp
            610                 615                 620
Asp Met Pro Asp Pro Gly Leu Val Leu Ala Gly Thr Lys Cys Ala Asp
625                 630                 635                 640
Gly Lys Ile Cys Leu Asn Arg Gln Cys Gln Asn Ile Ser Val Phe Gly
            645                 650                 655
Val His Glu Cys Ala Met Gln Cys His Gly Arg Gly Val Cys Asn Asn
            660                 665                 670
Arg Lys Asn Cys His Cys Glu Ala His Trp Ala Pro Pro Phe Cys Asp
            675                 680                 685
Lys Phe Gly Phe Gly Gly Ser Thr Asp Ser Gly Pro Ile Arg Gln Ala
            690                 695                 700
Glu Ala Arg Gln Glu Ala Ala Glu Ser Asn Arg Glu Arg Gly Gln Gly
705                 710                 715                 720
Gln Glu Pro Val Gly Ser Gln Glu His Ala Ser Thr Ala Ser Leu Thr
                    725                 730                 735
Leu Ile

<210> SEQ ID NO 5
<211> LENGTH: 2642
<212> TYPE: DNA
<213> ORGANISM: Homo sapiens

<400> SEQUENCE: 5
taaccaaggt ttaaccatag gaattctggt gaccatcctg tgtcttcttg ctgccggatt      60
tgtggtttat ctcaaaagga agaccttgat acgactgctg tttacaaata agaagaccac     120
cattgaaaaa ctaaggtgtg tgcgcccttc ccggccaccc cgtggcttcc aaccctgtca     180
ggctcacctc ggccaccttg aaaaggcct gatgaggaag ccgccagatt cctacccacc      240
gaaggacaat cccaggagat tgctgcagtg tcagaatgtt gacatcagca gacccctcaa     300
cggcctgaat gtccctcagc cccagtcaac tcagcgagtg cttcctcccc tccaccgggc     360
cccacgtgca cctagcgtcc ctgccagacc cctgccagcc aagcctgcac ttaggcaggc     420
ccaggggacc tgtaagccaa acccccctca gaagcctctg cctgcagatc ctctggccag     480
aacaactcgg ctcactcatg ccttggccag accccaggga caatgggaga ctgggctccg     540
cctggcaccc ctcagacctg ctccacaata tccacaccaa gtgccagat ccacccacac      600
cgcctatatt aagtgagaag ccgacaccttt ttttcaacag tgaagacaga agtttgcact    660
atctttcagc tccagttgga gttttttgta ccaacttta ggattttttt taatgtttaa     720
aacatcatta ctataagaac tttgagctac tgccgtcagt gctgtgctgt gctatggtgc     780
tctgtctact tgcacaggta cttgtaaatt attaattat gcagaatgtt gattacagtg      840
cagtgcgctg tagtaggcat ttttaccatc actgagtttt ccatggcagg aaggcttgtt     900
gtgcttttag tatttagtg aacttgaaat atcctgcttg atgggattct ggacaggatg      960
tgtttgcttt ctgatcaagg ccttattgga aagcagtccc ccaactaccc ccagctgtgc    1020
ttatggtacc agatgcagct caagagatcc caagtagaat ctcagttgat tttctggatt    1080
ccccatctca ggccagagcc aagggggcttc aggtccaggc tgtgtttggc tttcagggag   1140
```

-continued

```
gccctgtgcc ccttgacaac tggcaggcag gctcccaggg acacctggga gaaatctggc    1200
ttctggccag gaagctttgg tgagaacctg ggttgcagac aggaatctta aggtgtagcc    1260
acaccaggat agagactgga acactagaca agccagaact tgaccctgag ctgaccagcc    1320
gtgagcatgt ttggaagggg tctgtagtgt cactcaaggc ggtgcttgat agaaatgcca    1380
agcacttctt tttctcgctg tcctttctag agcactgcca ccagtaggtt atttagcttg    1440
ggaaaggtgg tgtttctgta agaaacctac tgcccaggca ctgcaaaccg ccacctccct    1500
atactgcttg gagctgagca aatcaccaca aactgtaata caatgatcct gtattcagac    1560
agatgaggac tttccatggg accacaacta ttttcagatg tgaaccatta accagatcta    1620
gtcaatcaag tctgtttact gcaaggttca acttattaac aattaggcag actctttatg    1680
cttgcaaaaa ctacaaccaa tggaatgtga tgttcatggg tatagttcat gtctgctatc    1740
attattcgta gatattggac aaagaacctt ctctatgggg catcctcttt ttccaacttg    1800
gctgcaggaa tctttaaaag atgcttttaa cagagtctga acctatttct taaacacttg    1860
caacctacct gttgagcatc acagaatgtg ataaggaaat caacttgctt atcaacttcc    1920
taaatattat gagatgtggc ttgggcagca tccccttgaa ctcttcactc ttcaaatgcc    1980
tgactaggga gccatgtttc acaaggtctt taaagtgact aatggcatga gaaatacaaa    2040
aatactcaga taaggtaaaa tgccatgatg cctctgtctt ctggactggt tttcacatta    2100
gaagacaatt gacaacagtt acataattca ctctgagtgt tttatgagaa agccttcttt    2160
tggggtcaac agttttccta tgctttgaaa cagaaaaata tgtaccaaga atcttggttt    2220
gccttccaga aaacaaaact gcatttcact ttcccggtgt tccccactgt atctaggcaa    2280
catagtattc atgactatgg ataaactaaa acgtgacac aaacacacac aaaagggaac    2340
ccagctctaa tacattccaa ctcgtatagc atgcatctgt ttattctata gttattaagt    2400
tctttaaaat gtaaagccat gctggaaaat aatactgctg agatacatac agaattactg    2460
taactgatta cacttggtaa ttgtactaaa gccaaacata tatatactat taaaaaggtt    2520
tacagaattt tatggtgcat tacgtgggca ttgtcttttt agatgcccaa atccttagat    2580
ctggcatgtt agcccttcct ccaattataa gaggatatga accaaaaaaa aaaaaaaaa     2640 aa                                                                   2642
```

<210> SEQ ID NO 6
<211> LENGTH: 205
<212> TYPE: PRT
<213> ORGANISM: Homo sapiens

<400> SEQUENCE: 6

```
Asp Asn Gln Gly Leu Thr Ile Gly Ile Leu Val Thr Ile Leu Cys Leu
1               5                   10                  15

Leu Ala Ala Gly Phe Val Val Tyr Leu Lys Arg Lys Thr Leu Ile Arg
            20                  25                  30

Leu Leu Phe Thr Asn Lys Lys Thr Thr Ile Glu Lys Leu Arg Cys Val
        35                  40                  45

Arg Pro Ser Arg Pro Arg Gly Phe Gln Pro Cys Gln Ala His Leu
    50                  55                  60

Gly His Leu Gly Lys Gly Leu Met Arg Lys Pro Asp Ser Tyr Pro
65                  70                  75                  80

Pro Lys Asp Asn Pro Arg Arg Leu Leu Gln Cys Gln Asn Val Asp Ile
                85                  90                  95
```

```
Ser Arg Pro Leu Asn Gly Leu Asn Val Pro Gln Pro Ser Thr Gln
        100                 105                 110

Arg Val Leu Pro Pro Leu His Arg Ala Pro Arg Ala Pro Ser Val Pro
        115                 120                 125

Ala Arg Pro Leu Pro Ala Lys Pro Ala Leu Arg Gln Ala Gln Gly Thr
    130                 135                 140

Cys Lys Pro Asn Pro Pro Gln Lys Pro Leu Pro Ala Asp Pro Leu Ala
145                 150                 155                 160

Arg Thr Thr Arg Leu Thr His Ala Leu Ala Arg Thr Pro Gly Gln Trp
                165                 170                 175

Glu Thr Gly Leu Arg Leu Ala Pro Leu Arg Pro Ala Pro Gln Tyr Pro
            180                 185                 190

His Gln Val Pro Arg Ser Thr His Thr Ala Tyr Ile Lys
            195                 200             205

<210> SEQ ID NO 7
<211> LENGTH: 908
<212> TYPE: DNA
<213> ORGANISM: Homo sapiens

<400> SEQUENCE: 7
agcaaggcag gaagctgcag agtccaacag ggagcgcggc cagggccagg agcccgtggg     60
atcgcaggag catgcgtcta ctgcctcact gacactcatc tgagccctcc catgacatgg    120
agaccgtgac cagtgctgct gcagaggagg tcacgcgtcc ccaaggcctc ctgtgactgg    180
cagcattgac tctgtggctt tgccatcgtt ccatgacaa cagacacaac acagttctcg    240
gggctcagga ggggaagtcc agcctaccag gcaggtctgc agaaacagtg caaggaaggg    300
cagcgacttc ctggttgagc ttctgctaaa acatggacat gcttcagtgc tgctcctgag    360
agagtagcag gttaccactc tggcaggccc cagccctgca gcaaggagga agaggactca    420
aaagtctggc ctttcactga gcctccacag cagtggggga gaagcaaggg ttgggcccag    480
tgtccccttt ccccagtgac acctccgcct tggcagccct gatgactggt ctctggctgc    540
aacttaatgc tctgatatgg cttttagcat ttattatatg aaaatagcag ggttttagtt    600
tttaatttat cagagaccct gccacccatt ccatctccat ccaagcaaac tgaatggcat    660
tgaaacaaac tggagaagaa ggtaggagaa agggcggtga actctggctc tttgctgtgg    720
acatgcgtga ccagcagtac tcaggtttga gggtttgcag aaagccaggg aacccacaga    780
gtcaccaacc cttcatttaa caagtaagaa tgttaaaaag tgaaacaat gtaagagcct    840 aactccatcc cccgtggcca ttactgcata aaaatagagt gcattttgaa ataaaaaaa    900 aaaaaaaa                                                             908

<210> SEQ ID NO 8
<211> LENGTH: 34
<212> TYPE: PRT
<213> ORGANISM: Homo sapiens

<400> SEQUENCE: 8

Glu Ala Arg Gln Glu Ala Ala Glu Ser Asn Arg Glu Arg Gly Gln Gly
1               5                   10                  15

Gln Glu Pro Val Gly Ser Gln Glu His Ala Ser Thr Ala Ser Leu Thr
            20                  25                  30

Leu Ile

<210> SEQ ID NO 9
```

```
<211> LENGTH: 23
<212> TYPE: DNA
<213> ORGANISM: Homo sapiens

<400> SEQUENCE: 9
cctgtgacct cccagagttc tgc                                              23

<210> SEQ ID NO 10
<211> LENGTH: 23
<212> TYPE: DNA
<213> ORGANISM: Homo sapiens

<400> SEQUENCE: 10
gaattcctat ggttaaacct tgg                                              23

<210> SEQ ID NO 11
<211> LENGTH: 24
<212> TYPE: DNA
<213> ORGANISM: Homo sapiens

<400> SEQUENCE: 11
cttgctgccg gatttgtggt ttat                                             24

<210> SEQ ID NO 12
<211> LENGTH: 24
<212> TYPE: DNA
<213> ORGANISM: Homo sapiens

<400> SEQUENCE: 12
agttgactgg ggctgaggga catt                                             24

<210> SEQ ID NO 13
<211> LENGTH: 23
<212> TYPE: DNA
<213> ORGANISM: Homo sapiens
<220> FEATURE:
<221> NAME/KEY: misc_feature
<222> LOCATION: (15)..(15)
<223> OTHER INFORMATION: Mismatch (g instead of c)

<400> SEQUENCE: 13
ggactctgca gcttgctgcc ttg                                              23

<210> SEQ ID NO 14
<211> LENGTH: 23
<212> TYPE: DNA
<213> ORGANISM: Homo sapiens

<400> SEQUENCE: 14
ggactctgca gcttcctgcc ttg                                              23

<210> SEQ ID NO 15
<211> LENGTH: 21
<212> TYPE: DNA
<213> ORGANISM: Homo sapiens

<400> SEQUENCE: 15
tcggggctca ggaggggaag t                                                21

<210> SEQ ID NO 16
<211> LENGTH: 21
<212> TYPE: DNA
<213> ORGANISM: Homo sapiens

<400> SEQUENCE: 16
```

```
-continued ggctgccaag gcggaggtgt c                                              21

<210> SEQ ID NO 17
<211> LENGTH: 24
<212> TYPE: DNA
<213> ORGANISM: Homo sapiens

<400> SEQUENCE: 17
ggccgggtga tctttggtct cttc                                           24

<210> SEQ ID NO 18
<211> LENGTH: 24
<212> TYPE: DNA
<213> ORGANISM: Homo sapiens

<400> SEQUENCE: 18
cccggctgtc tgtcttggtg ctct                                           24

<210> SEQ ID NO 19
<211> LENGTH: 21
<212> TYPE: DNA
<213> ORGANISM: Homo sapiens

<400> SEQUENCE: 19
ctgctgagat gggaaagggc t                                              21

<210> SEQ ID NO 20
<211> LENGTH: 21
<212> TYPE: DNA
<213> ORGANISM: Homo sapiens

<400> SEQUENCE: 20
ttcaggataa tcacctgagc a                                              21
```

USE OF ADAM 12 FOR DIAGNOSIS AND THERAPY OF PREECLAMPSIA

CROSS-REFERENCE TO RELATED APPLICATIONS

This Application is the National Phase of PCT/EP2004/011632, filed Oct. 15, 2004, and published as WO 2005/040831, which in turn claims priority from European Patent Application No. 03023815.8, filed Oct. 17, 2003, the contents of these applications are incorporated herein by reference.

The present invention relates to the use of ADAM 12, particularly ADAM 12-S, for diagnosis and therapy of preeclampsia and related syndromes.

Preeclampsia (also known as toxemia or eclampsism) is a disorder or syndrome affecting about 5% of pregnant women. It becomes manifest in the last trimester of pregnancy and is characterized by high blood pressure, protein in the urine, and—sometimes—swelling (edema) of the face and hands. Preeclampsia may also include sudden weight gain, blurred vision, severe headaches, dizziness, and stomach pain.

In preeclampsia, the trophoblast (embryonic tissue that invades the uterus wall to form the embryonic part of the placenta) is poorly differentiated and shows incomplete invasion of the uterus wall.

When left untreated, preeclampsia can lead to severe problems, endangering both mother and fetus. High blood pressure constricts the blood vessels in the uterus that supply the fetus with oxygen and nutrients. The fetal growth is retarded. Preeclampsia can increase the risk of placental abruption (separation of the placenta from the uterus wall) before delivery, risk of kidney failure, cerebral hemorrhage, intravascular coagulation, lung edema, and circulatory collapse.

Furthermore, untreated preeclampsia can lead to a related life-threatening condition, eclampsia. Eclampsia can lead to convulsions and coma. The HELLP (hemolysis, elevated liver enzymes, and low platelet count) syndrome is also frequently considered to be related to preeclampsia, as preeclampsia is thought to increase the risk for HELLP. HELLP is characterized by destruction of red blood cells, liver damage, and a reduction in the number of blood platelets. Thus, also HELLP can be life-threatening.

Intrauterine growth retardation (small for gestational age (SGA) infants) is another syndrome related to preeclampsia, as it is associated with poor trophoblast differentiation and growth retardation of the embryo.

Pregnancy induced hypertension (PM) is also a syndrome related to preeclampsia. It is characterized by high blood pressure, but lacks the proteinuria characteristic for preeclampsia.

Other syndromes related to preeclampsia are superimposed gestosis ("Aufpropfgestose") and gestational diabetes.

A causal treatment of preeclampsia and said related syndromes is not available. The usual treatment consists of the treatment of hypertension, intravenious magnesia to prevent eclamptic convulsions and corticosteroids in case of HELLP syndrome. Very often symptoms can not be controlled and preterm delivery is the only way to save the life of mother and child. Preterm delivery is still associated with a high morbidity and mortality of the child.

Currently, diagnosis of preeclampsia is limited to relatively late arising symptoms such as blood pressure (typically above 140/90 mm Hg) and protein content of the urine (proteinuria, typically more than 0.3 g/24 hours or a level of 2+ by dipstick test). Another sign for preeclampsia is glomerular endotheliosis, a histological change of the kidney which can be observed in kidney biopsies of 50% of the patients. These markers are relatively unreliable or become manifest only at later stages of preeclampsia. Similarly, said related syndromes can not be diagnosed in a satisfactory manner. In summary, there remains an urgent need for molecular markers indicative of preeclampsia (Beaulieu, M. D., Prevention of preeclampsia. In: Canadian Task Force on the Periodic Health Examination. Canadian Guide to Clinical Preventive Health Care. Ottawa: Health Canada, 1994; 136-43).

A small number of genes has been reported to be either upregulated (EPAS-1/HIF-2α, neurokinin B, TIMP-1, VEGFR-1 (=sFLT-1), VEGF, IGFBP-1, IGFBP-3, matrix metalloproteinase-2, leptin, plasminogen activator inhibitor 1 (PAI-1)) or down-regulated (IGF-1, angiopoetin-2, decorin, various ephrins, PIGF, HLA-G) during preeclampsia. PIGF has been reported to be downregulated in blood serum, but not in placental tissue. HB-EGF, various ephrins, and TGF-133 have also been discussed as being de-regulated during preeclampsia.

However, most of these genes are only weakly up- or downregulated and/or can only be measured in placental tissue, requiring to take placenta tissue samples for analysis. Thus, frequent measurements at short time intervals are not possible. In any case, none of the genes cited above have been put into practice as routine markers for preeclampsia or related syndromes.

Consequently, a reliable diagnosis of preeclampsia or related syndromes is not possible at the moment. However, reliable diagnosis of onset and progression of said disorders or syndromes would allow to develop better treatment and to evaluate the risk for mother and fetus at each stage of pregnancy. Reliable diagnosis is also needed, because women experience no obvious symptoms at early stages of preeclampsia or related syndromes.

Therefore, there is a persistent need for molecular markers of preeclampsia or related syndromes. Such markers would also be useful to identify and classify different subtypes of preeclampsia and related syndromes.

Consequently, the problem underlying the present invention resides in improving diagnosis of preeclampsia or related syndromes. In particular, the problem resides in providing a marker more indicative of preeclampsia and/or related syndromes than other markers. In particular, the problem resides in providing a highly indicative marker that can also be measured in body fluids.

Another problem underlying the present invention resides in providing treatment of preeclampsia and/or related syndromes.

With respect to diagnosis, the problem is solved by use of the expression level of a peptide or polypeptide with a sequence selected from the group consisting of
a) an amino acid sequence as presented in SEQ ID NO: 2 or 4;
b) an amino acid sequence exhibiting a sequence identity with any of the amino acid sequences according to a) of at least 85% over 100 amino acid residues;
c) a fragment of any of the sequences defined above for diagnosis of preeclampsia or a related syndrome.

The problem is also solved by use of a nucleic acid molecule comprising a nucleic acid selected from the group consisting of
a) a nucleic acid with a sequence as presented in SEQ ID NO: 1 or 3;
b) a nucleic acid with a sequence that exhibits a sequence identity with any of the sequences defined in a) of at least 70% over 300 residues;
c) a nucleic acid which is capable of hybridizing with the nucleic acid as defined in a), or b) under conditions of medium or high stringency;
d) a nucleic acid with the antisense-sequence of any of the sequences defined in a), b) or c);
e) a fragment of any of the nucleic acids as defined in a), b), c), or d);

f) an RNA corresponding to any of the sequences defined in a), b), c), d) or e);

for diagnosis of preeclampsia or a related syndrome.

Furthermore, the problem is solved by use of a ligand binding specifically to a peptide or polypeptide with a sequence selected from the group consisting of
 a) an amino acid sequence as presented in SEQ ID NO: 2 or 4;
 b) an amino acid sequence exhibiting a sequence identity with any of the amino acid sequences according to a) of at least 85% over 100 amino acid residues;
 c) a fragment of any of the sequences defined above for diagnosis of preeclampsia or a related syndrome.

For reference, the individual SEQ ID NO denotes the following sequence:
SEQ ID NO: 1 nucleotide sequence of the human ADAM 12-L cDNA
SEQ ID NO: 2 protein sequence of the human ADAM 12-L protein
SEQ ID NO: 3 nucleotide sequence of the human ADAM 12-S cDNA
SEQ ID NO: 4 protein sequence of the human ADAM 12-S protein
SEQ ID NO: 5 nucleotide sequence region specific for the human ADAM 12-L cDNA
SEQ ID NO: 6 protein sequence region specific for human ADAM 12-L
SEQ ID NO: 7 nucleotide sequence region specific for the human ADAM 12-S cDNA
SEQ ID NO: 8 protein sequence region specific for human ADAM 12-S
SEQ ID NO: 9 PCR primer (1), ADAM 12 5' primer
SEQ ID NO: 10 PCR primer (2), ADAM 12-L 3' primer
SEQ ID NO: 11 PCR primer (3), ADAM 12-L 5' primer
SEQ ID NO: 12 PCR primer (4), ADAM 12-L 3' primer
SEQ ID NO: 13 PCR primer (5), ADAM 12-S 3' primer, containing a single nucleotide exchange (G instead of C) at position 15.
SEQ ID NO: 14 PCR primer (6), ADAM 12-S 3' primer, correct sequence
SEQ ID NO: 15 PCR primer (7), ADAM 12-S 5' primer
SEQ ID NO: 16 PCR primer (8), ADAM 12-S 3' primer
SEQ ID NO: 17 PCR primer (9), human cyclophilin B 5' primer
SEQ ID NO: 18 PCR primer (10), human cyclophilin B 3' primer
SEQ ID NO: 19 PCR primer (11), EF-1α 5' primer
SEQ ID NO: 20 PCR primer (12), EF-1α 3' primer SEQ ID NO: 1 to 16 refer to nucleic acids, peptides or polypeptides derived from ADAM 12. ADAM 12 (meltrin alpha) is a member of the ADAM (a disintegrin and metalloprotease) family. Human ADAM 12 exists in two isoforms, a longer membrane anchored isoform, ADAM 12-L (SEQ ID NO: 1, 2, GenBank Acc. No. AF023476) and a shorter secreted isoform, ADAM 12-S (SEQ ID NO: 3, 4, GenBank Acc. No. AF023477). In the literature, the gene names may be spelled slightly differently, e.g. ADAM-12S, meltrin α.

ADAM 12 has been implicated in cell adhesion and muscle cell differentiation and fusion. Additionally, ADAM 12 has been implicated in fat tissue development and it is upregulated in several types of human carcinomas. ADAM 12-S is expressed highly in the placenta and can be detected in blood serum during pregnancy, while it is undetectable in non-pregnancy serum. However, no connection of ADAM 12, particularly ADAM 12-S, to preeclampsia or a related syndrome has been reported previously.

As a consequence of the present invention it is known that expression, particularly transcription, of ADAM 12 is strongly upregulated in preeclampsia. In a comparison with 1600 known genes examined by gene array analysis, ADAM 12 was found to be the most strongly upregulated gene (Example 8). Therefore, ADAM 12 can be considered a valuable diagnostic marker, and upregulation of ADAM 12 can be used to diagnose preeclampsia and related syndromes. ADAM 12, particularly ADAM 12-S, is present in body fluids such as blood. Blood samples are taken routinely at physical examinations during most pregnancies. Thus, it is possible to routinely monitor pregnant mothers at short intervals for upregulation of ADAM 12, allowing to early detect and monitor preeclampsia or related disorders with minimal effort and risk for the mother.

"Nucleic acid" according to the present invention relates to all known nucleic acids such as DNA, RNA, peptide nucleic acids, morpholinos, and nucleic acids with backbones other than phosphodiesters, such as phosphothioates or phosphoramidates. The person skilled in the art knows which nucleic acids are best suited for a particular purpose, such as diagnosis, or a particular method (such as Northern hybridization or polymerase chain reaction (PCR)).

Unless otherwise specified, the manipulations of nucleic acids and polypeptides/-proteins can be performed using standard methods of molecular biology and immunology (see, e.g. Maniatis et al. (1989), Molecular cloning: A laboratory manual, Cold Spring Harbor Lab., Cold Spring Harbor, N.Y.; Ausubel, F. M. et al. (eds.) "Current protocols in Molecular Biology". John Wiley and Sons, 1995; Tijssen, P., Practice and Theory of Enzyme Immunoassays, Elsevier Press, Amsterdam, Oxford, N.Y., 1985).

The term "comprise" preferably refers to nucleic acid molecules in which the nucleic acids with the described sequences are functionally relevant, e.g. for diagnostic use or therapeutic use, such as vectors for therapeutical use or expression of corresponding RNAs or proteins. For example, the above defined nucleic acids may be part of a vector allowing transcription of antisense DNA or RNA probes. Preferably, any additional nucleic acids upstream or downstream of the nucleic acid are not longer than 80 kb, more preferably not longer than 20 kb, more preferably not longer than 5 kb. More preferably, the term "comprise" does not relate to large constructs accidentally including the sequence, such as genomic BAC or YAC clones. More preferably, the nucleic acid molecule consists of the above defined nucleic acids.

Preferably, the nucleic acid molecule is purified and/or isolated. Suitable purification methods, including gel electrophoresis and capillary electrophoresis, are well known in the art. An isolated nucleic acid molecule is understood as a nucleic acid molecule isolated from the human or animal body or gained by means of a technical process, such as a microbiological process or organic synthesis.

In a preferred embodiment, said nucleic acid molecule comprises a nucleic acid with a sequence selected from the group of sequences as presented in SEQ ID NO: 1 or 3. SEQ ID NO: 1 corresponds to the sequence presented in GenBank Acc. No. AF023476, and SEQ ID NO: 3 corresponds to the sequence presented in GenBank Acc. No. AF023477.

In another preferred embodiment, said nucleic acid molecule comprises a nucleic acid with a sequence that exhibits a sequence identity with any of the sequences defined above of at least 70%, preferably at least 80%, more preferably at least 90%, and most preferred of at least 95% over 300 nucleotide residues.

"Sequence identity" refers to the degree of identity (% identity) of two sequences that in the in the case of peptides or polypeptides can be determined by means of for example BLASTP 2.0.1 and in the case of nucleic acids can be determined by means of for example BLASTN 1.014, wherein the Filter is set off and BLOSUM is 62 (Altschul et al., Nucleic Acids Res., 25:3389-3402).

Such nucleic acids include those whose sequences deviate from the above defined sequences due to the degeneration of the genetic code, the presence of different alleles in the human or animal population, and the presence of related sequences in different species. Such nucleic acids can still be used according to the present invention.

In another preferred embodiment, the nucleic acid molecule comprises a nucleic acid capable of hybridizing with the nucleic acids according to SEQ ID NO: 1 or 3 under conditions of low, preferably medium, or, more preferred, high stringency.

In such hybrids, duplex formation and stability depend on substantial complementarity between the two strands of the hybrid and a certain degree of mismatch can be tolerated. Therefore, the nucleic acids and nucleic acid probes of the present invention may include mutations (both single and multiple), deletions, insertions of the above-identified sequences, and combination thereof, as long as that nucleic acids still have substantial sequence similarity to the original sequence which permits the formation of stable hybrids with the target nucleotide sequence of interest. For example, a single nucleotide mismatch in PCR primer (SEQ ID NO: 13) as compared to the correct primer sequence (SEQ ID NO: 14) was found to be tolerable.

Suitable experimental conditions for determining whether a given DNA or RNA sequence "hybridizes" to a specified polynucleotide or oligonucleotide probe involve presoaking of the filter containing the DNA or RNA to examine for hybridization in 5×SSC (sodium chloride/sodium citrate) buffer for 10 minutes, and prehybridization of the filter in a solution of 5×SSC, 5×Denhardt's solution, 0.5% SDS and 100 mg/ml of denaturated sonicated salmon sperm DNA (Maniatis et al., 1989, see above), followed by hybridization in the same solution containing a concentration of 10 ng/ml of a random primed (Feinberg, A. P. and Vogelstein, B. (1983), Anal. Biochem. 132:6-13), $^{32}$P-dCTP-labeled (specific activity >1×10$^9$ cpm/µg) probe for 12 hours at approximately 45° C. The filter is then washed twice for 30 minutes in 2×SSC, 0.5% SDS at least 55° C. (low stringency), at least 60° C. (medium stringency), preferably at least 65° C. (medium/high stringency), more preferably at least 70° C. (high stringency) or most preferably at least 75° C. (very high stringency). Molecules to which the probe hybridizes under the chosen conditions are detected using an x-ray film or a "phosphor imager".

In another preferred embodiment, said nucleic acid molecule comprises a nucleic acid which is capable of hybridizing with the nucleic acids according to SEQ ID NO: 1 or 3, but not capable of hybridizing with nucleic acids encoding ADAM 19 or ADAM 33.

Preferably, the nucleic acids should be chosen from sequence regions specific for the above-defined sequences, i.e. the nucleic acids should not cross-hybridize with nucleic acids encoding other genes, particularly other metalloprotease genes, more particularly ADAMs (Seals, D. F, and Courtneidge, S. A. (2003). The ADAMs family of metalloproteases: multidomain proteins with multiple functions. Genes & Dev. 17, 7-30), even more particularly ADAM 19 (GenBank Acc. No. Y13786) or ADAM 33 (GenBank Acc. No. AB009672, most particularly ADAM 2 (fertilin beta, GenBank Acc. Nos. AJ133005 or NM 001464) (see also Yoshinaka, T., Nishii, K., Yamada, K., Sawada, H., Nishiwaki, E., Smith, K., Yoshino, K., Ishiguro, H., and Higashiyama, S. (2002). Identification and characterization of novel mouse and human ADAM 33s with potential metalloprotease activity. Gene 282, 227-236), under the applied conditions, preferably conditions of medium, medium/high, high or very high stringency.

In another preferred embodiment, the nucleic acid molecule comprises a nucleic acid with the antisense-sequence of any of the sequences defined above.

In another preferred embodiment, the nucleic acid molecule comprises a nucleic acid which is a fragment of any of the nucleic acids as defined above.

The term "fragment" as used according to the present invention can have different meanings depending on the molecule and purpose referred to. A person skilled in the art knows how to choose appropriate fragments for the relevant purpose. In particular, the person skilled in the art knows how to choose fragments of appropriate length and suitable sequence (see also Examples 9 and 10).

Preferably, the fragments should be chosen from sequence regions specific for the above-defined sequences, i.e. the chosen fragments should not cross-hybridize with nucleic acids encoding other genes, particularly other metalloprotease genes, more particularly ADAMs, even more particularly ADAM 19 or ADAM 33, most particularly ADAM 2, under the applied conditions. Sequence regions specific for the above defined sequences can be determined easily by the person skilled in the art, e.g. by database searches and sequence comparisons. Such searches and comparisons are routine in the art and possible using sequence analysis programs such as BLAST and ClustalW. Preferably, the fragments should be chosen from regions of high complexity which can be determined by low complexity filters available in standard sequence analysis programs. Specificity for the purpose of the present invention may also be achieved in spite of cross-hybridization, if the investigated sequences can still be measured unequivocally, e.g. by the size of amplified PCR products. Therefore, such fragments, particularly PCR primers, can still be used according to the present invention.

In another preferred embodiment, the fragment has a sequence consisting of or being part of any of SEQ ID NO: 5, 7, 9, 10, 11, 12, 13, 14, 15, 16;

In another preferred embodiment, the fragment should be at least 12, preferably at least 15, more preferably at least 19, even more preferably at least 30 nucleotides in length.

In another preferred embodiment, said nucleic acid molecule comprises an RNA corresponding to any of the sequences defined above. RNA molecules are frequently used as probes for analysis of nucleic acids and measurement of gene expression, e.g by in situ hybridization or RNAse protection assays. A suitable RNA in situ hybridization probe may, for example, comprise or consist of the 667 nucleotide sequence fragment corresponding to the antisense sequence of position 1769 to 2445 in SEQ ID NO: 3.

Diagnosis according to the present invention includes monitoring, confirmation, subclassification and prediction of the relevant disorder or syndrome. Monitoring relates to monitoring of an already diagnosed disorder, e.g. to analyze the progression of the disorder or the influence of a particular treatment on the progression of disorder. Confirmation relates to the confirmation or substantiation of a diagnosis already performed using other indicators, symptoms, or markers. Subclassification relates to further defining a diagnosis according to different subclasses of the diagnosed disorder, e.g. defining according to mild and severe forms of the disorder. Prediction relates to predicting a disorder before other symptoms or markers have become evident or have become significantly altered. Prediction also relates to classifying patients into groups of low, medium, or high risk of developing the disorder.

In another preferred embodiment, diagnosis relates to the diagnosis of syndromes related to preeclampsia.

According to the present invention, syndromes "related" to preeclampsia include other pregnancy-associated disorders or syndromes with similar aetiology and/or symptoms as preeclampsia. Particularly included are eclampsia, pregnancy induced hypertension, HELLP syndrome, intrauterine growth retardation and superimposed gestosis. Most particularly, related syndromes are eclampsia, pregnancy induced hypertension, HELLP syndrome, and superimposed gestosis.

For diagnosis of preeclampsia or related syndromes, preferably the expression level or amount of ADAM 12 RNA or its corresponding protein is determined. The term "measuring" according to the present invention relates to determining the amount or activity, preferably semi-quantitatively or quantitatively, of the substance in question. Measuring is frequently done indirectly, through measuring of ligands, labels, or enzymatic reaction products.

ADAM 12 expression can be measured in tissue samples and body fluid samples. A tissue sample refers to any kind of tissue obtained from the dead or alive human or animal body, particularly a placental tissue sample, more particularly a human placental tissue sample (e.g. cytotrophoblast or syncytiotrophoblast cells). Body fluid according to the present invention refers to any kind of body fluid, particularly to blood (including plasma, serum, uterine vein blood or uterine vein blood smears), amniotic fluid, lymphe, cerebral liquor, urine, and saliva, more particularly to blood, amniotic fluid, and urine, most particularly to blood. Expression according to the present invention includes transcription, translation and transcript or protein stability.

RNA can be measured easily and quantitatively by methods known to the person skilled in the art. RNA can be obtained or isolated by purification methods known in the art, e.g. involving steps of enzymatic digestion of tissue or proteins, and phenol/chloroform/isoamylalcohol extraction.

Suitable methods for measuring ADAM 12 expression, particularly ADAM 12 RNA (transcript), include the hybridization of nucleic acid probes, such as in situ hybridizations, Northern hybridizations, RNAse protection assays, gene arrays, RT-PCR, and other suitable methods known in the art. Preferably, a method allowing quantitative or semi-quantitative measurement, such as quantitative RT-PCR, is chosen.

Characteristics of suitable nucleic acid probes, e.g. in situ hybridization probes or PCR primers, are known in the art. The probes may be based on DNA, RNA or derivatives thereof such as peptide nucleic acids. The probes may be synthesized by use of DNA synthesizers according to standard procedures or, preferably for long sequences, by use of PCR technology with a selected template sequence and selected primers. Depending on the procedure, the nucleic acid probes may be labeled with any suitable substances known in the art, such as digoxigenin, biotin, or thyroxin (as targets of a secondary ligands, particularly a secondary antibody or a fragment thereof), luminescent or fluorescent labels (e.g. fluorescein) and radioactive isotopes ($^{32}P$, $^{125}I$, $^{35}S$, and the like). A probe labeled with a radioactive isotope can be constructed from a DNA template by a conventional nick translation reaction or by randomly primed polymerization. The probe may also be labeled at both ends with different types of labels, for example with an isotopic label at one end and a biotin label at the other end. The labeled probe and sample can then be combined in a hybridization buffer solution and held at an appropriate temperature until annealing occurs.

Although gene transcripts are usually present only within cells, ADAM 12 RNA can also be measured (at lower levels) in body fluids, particularly in blood samples, including blood plasma and serum, by methods known in the art (Ng, E.K.O., Tsui, N. B. Y., et al. (2003).

Messenger RNA of placental origin is readily detectable in maternal plasma. Proc Natl Acad Sci USA, vol. 100(8):4748-53 and Ng, E.K.O., Leung, T. N., et al. (2003). The concentration of circulating Corticotropin-releasing hormone RNA in maternal plasma is increased in preeclampsia. Clin. Chem. 49, 727-731). According to the present invention, blood plasma is the fluid part of the blood, it lacks the corpuscular components such as blood cells and platelets. Blood serum is blood plasma additionally lacking fibrinogen.

Diagnosis is preferably performed in vitro, i.e. using elements isolated from the body. Tissue samples and body fluid samples can be obtained by laboratory assistants trained for this purpose during routine examinations. Body fluid and tissue samples can be obtained by any method known to the person skilled in the art, including amniocentesis and biopsy (particularly chorion villi biopsy). In particular, blood samples are taken routinely at physical examinations during most pregnancies.

Routine examinations are typically performed in 4' week intervals during the first two trimenons, and biweekly during the last trimenon. Typically, blood samples are taken in week 13 and at least once between weeks 21 and 28 of pregnancy. However, many pregnant women come to examinations on a bi-weekly or weekly basis, particularly during the last half of pregnancy.

Thus, it is possible to routinely monitor pregnant women at short intervals for upregulation of ADAM 12, allowing to early detect and monitor preeclampsia or related disorders with minimal effort and risk for mother and fetus.

Levels (amounts) of ADAM 12 expression indicative or of diagnostic value for preeclampsia and its related syndromes can be detected by comparing expression levels under healthy conditions with expression levels under sick conditions (conditions of the existing or developing relevant disorder or syndrome). For example, the levels under sick conditions can be determined relative to a healthy control group, or relative the mean population of pregnant mothers, or relative to earlier measurements for the same person.

In the present invention, approximately 4 to 5-fold increases of ADAM 12 transcript levels as measured by quantitative Real-Time RT-PCR were found to be correlated with preeclampsia (see Example 10). The transcript levels were increased in placental tissue of both maternal and fetal origin (maternal side and fetal side of the placenta).

Further levels of ADAM 12 expression indicative of preeclampsia and related syndromes can be determined in more detail in clinical screenings as known in the art. For example, a level deviating from the average level (e.g. the mean level of the entire investigated group) by more than two standard deviations, preferably by more than three standard deviations may be considered indicative of the analyzed disorder. Deviations indicative of preeclampsia or a related syndrome may be even smaller, if additional markers indicative of the disorder are also deviating from the average level. More weakly deviating levels may be used to classify a person into a medium or high risk group of developing the disorder. Those markers may include blood pressure, protein content in the urine and molecular markers. Additional factors may influence the diagnosis, e.g. the regular blood pressure or the number of previous pregnancies in a given patient. Usually, the highest risk for preeclampsia is during the first pregnancy. Thus, measuring ADAM 12 expression yields a diagnostic parameter that is preferably compared with additional parameters to allow a decision about a necessary treatment.

The present invention also relates to a method of diagnosis of preeclampsia in which the above defined nucleic acid molecules or the expression level(s) thereof are used.

In another preferred embodiment, the fragment has a sequence consisting of or being part of SEQ ID NO: 7, 13, 14, 15, 16.

In another preferred embodiment, the fragment has a sequence consisting of or being part of SEQ ID NO: 5 or 10, 11, 12.

SEQ ID NO: 7, 13, 14, 15, and 16 are unique (specific) to the splice variant ADAM 12-S. SEQ ID NO: 5 or 10, 11, 12 are unique (specific) to the splice variant ADAM 12-L. Both splice variants, ADAM 12-L and ADAM 12-S, are upregulated in preeclampsia. However, the splice variants show different regulation properties. In a control group, the level of ADAM 12-L RNA was found to be close to zero, whereas ADAM 12-S showed a measurable basal expression level (both measured by semi-quantitative RT-PCR). Also, the total (upregulated) level of ADAM 12-L RNA in preeclampsia was lower than the one of ADAM 12-S RNA.

For specific detection of mRNA encoding the long splice variant, ADAM 12-L, or the short splice variant, ADAM 12-S, the probe should be directed against the sequence regions unique to these splice variants. For example, probes may be directed against the unique 3'-ends of ADAM 12-L (SEQ ID NO: 5) and ADAM 12-S (SEQ ID NO: 7). As known to the person skilled in the art, a short overlap of the probes with regions common to both splice variants may be tolerable without loss of specificity. For example, the 5' ends of PCR primers may be located in sequence regions common to both transcripts. It is also sufficient if only one of the two primers is located in the regions unique to each splice variant. E.g., the primer according to SEQ ID NO: 9 may be used in combination with the primers according to SEQ ID NO: 13, 14, or 16 to amplify a product specific for ADAM 12-S.

As mentioned above, the invention also relates to the use of the expression level of a peptide or polypeptide as defined above.

Furthermore, the invention also relates to the use of a ligand binding a peptide or polypeptide as defined above.

Thus, the present invention also relates to the measurement of ADAM 12 protein. In another preferred embodiment, the biological activity of ADAM 12 is measured. ADAM 12 protein or biological activity can be measured in tissue samples, e.g. in placental tissue samples or other samples taken from the patient.

ADAM 12, particularly ADAM 12-S, is also present in body fluids, particularly the blood (Shi, Z., Xu, W., Loechel, F., Wewers, U. M., and Murphy, L. J. (2000). ADAM 12, a disintegrin metalloprotease, interacts with insulin-like growth factor-binding protein-3. J. Biol. Chem. 275, 18574-18580; Gilpin, B. J., Loechel, F., Maffei, M.-G., Engvall, E., Albrechtsen, R., and Wewer, U. M. (1998). A Novel, Secreted Form of human ADAM 12 (Meltrin alpha) Provokes Myogenesis in Vivo. J. Biol. Chem. 273, 157-166). Therefore, ADAM 12-S amount or level of biological activity can easily be measured in body fluids, particularly in blood, blood plasma or blood serum.

Biological activity according to the present invention relates to any activity exerted by ADAM 12, ADAM 12-L or ADAM 12-S in the human or animal body. In particular, biological activity relates to proteolytic activity, in particular to proteolytic activity exerted against HB-EGF, P-LAP (placental leucine aminopeptidase, identical to cystine aminopeptidase) IGFBP-3, or IGFBP-5. According to the present invention, the term "biological activity" also relates to any effects, particularly undesired or toxic effects, exerted by ADAM 12, ADAM 12-L, or ADAM 12-S if they are more highly expressed or more active than usual.

In a preferred embodiment, the peptide or polypeptide may comprise a sequence selected from the amino acid sequences presented in SEQ ID NO: 2 or 4. SEQ ID NO: 2 corresponds to the sequence presented in GenBank Acc. No. AF023476 and SEQ ID NO: 4 corresponds to the sequence presented in GenBank Acc. No. AF023477.

In another preferred embodiment, said peptide or polypeptide has a sequence exhibiting a sequence identity with any of the amino acid sequences defined above of at least 85%, preferably 90%, more preferably 95% over 100 amino acid residues.

In another preferred embodiment, said peptide or polypeptide has a sequence which is a fragment of any of the amino acid sequences defined above.

The above defined peptide or polypeptide may also be part of fusion peptides or polypeptides. In such fusions another peptide or polypeptide may be fused at the N-terminus or the C-terminus of the peptide or polypeptide of interest. A fusion can be produced by fusing a nucleic acid sequence (or a portion thereof) encoding another polypeptide to a nucleic acid sequence (or a portion thereof) of the present invention. Techniques for producing fusion polypeptides are known in the art and include ligating the coding sequences so that they are in frame and the expression of the fusion polypeptide is under control of the same promotor(s) and terminator.

With respect to diagnosis, the definitions given above for the use of nucleic acids apply analogously.

Suitable methods for measurement of ADAM 12 are known to the person skilled in the art. For example, measurement can be done indirectly, through measuring of cellular responses, the amount of bound ligands, labels, or enzymatic reaction products.

For measuring cellular responses, the sample or processed sample is added to a cell culture and an internal or external cellular response is measured. The cellular response may include the expression of a reporter gene or the secretion of a substance, e.g. a peptide, polypeptide, or a small molecule.

Other preferred methods for measurement may include measuring the amount of a ligand binding specifically to the ADAM 12 proteins, peptides or polypeptides. Binding according to the present invention includes both covalent and non-covalent binding.

A ligand according to the present invention can be any peptide, polypeptide, nucleic acid, or other substance (including small molecules) binding to peptides, polypeptides with the above described sequences. It is well known that the above-defined peptides or polypeptides, if obtained or purified from the human or animal body, can be modified, e.g. by glycosylation. A suitable ligand according to the present invention may bind these peptides or polypeptides also via such sites.

Preferably, the ligand should bind specifically to said peptides or polypeptides. "Specific binding" according to the present invention means that the ligand should not bind substantially to ("cross-react" with) another protein, isoform or substance present in the sample investigated. Preferably, the specifically bound protein or isoform should be bound with at least 3 times higher, more preferably at least 10 times higher and even more preferably at least 50 times higher affinity than any other relevant protein, isoform, or substance. Other relevant proteins may include other ADAMs, particularly ADAM 2, more particularly ADAM 19 or ADAM 33.

Non-specific binding may be tolerable, particularly if the investigated ADAM 12 proteins or isoforms can still be distinguished and measured unequivocally, e.g. according to their size on a Western Blot, or by their relatively higher abundance in the sample.

Binding of the ligand can be measured by any method known in the art. Preferably, the method is semi-quantitative or quantitative. Suitable methods are described in the following.

If the ligand does not only bind, but also serves as a substrate of the above-defined peptides or polypeptides, the reaction product may be measured directly (e.g. cleaving of HB- EGF, P-LAP, IGFBP-3, or IGFBP-5 as a substrate may be measured by analyzing the cleaved product, e.g. on a Western Blot or by ELISA).

Furthermore, the ligand may be coupled covalently or non-covalently to a label allowing detection and measurement of the ligand.

Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often advantageous to increase the signal. Suitable secondary and higher order ligands may include antibodies, secondary antibodies, and the well-known streptavidin-biotin system (Vector Laboratories, Inc.)

The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, and the like. In the case of a peptide or polypeptide, the tag is preferably at the N-terminus and/or C-terminus.

Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels.

Enzymatically active labels include e.g. hydrogen peroxidase, alkaline phosphatase, and derivatives thereof. Suitable substrates for detection of these enzymes include di-aminobenzidine (DAB), NBT-BCIP (4-nitro blue tetrazolium chloride and 5-bromo-4-chloro-3-indolyl-phosphate, available as ready-made stock solution from Roche Diagnostics), and CDP-Star™ (Amersham). Suitable enzyme-substrate combinations result e.g. in colored reaction products, fluorescence or chemoluminescence. Typical fluorescent labels include Cy3, Cy5, Texas Red, Fluorescein, and the Alexa dyes (e.g. Alexa 568). Typical radioactive labels include $^{35}S$, $^{125}I$, $^{32}P$ and the like.

Suitable measurement methods according the present invention also include electrochemiluminescence (electrogenerated chemiluminescence), ELISA (enzyme-linked immunosorbent assay), sandwich enzyme immune tests, turbidimetry, nephelometry, latex-enhanced turbidimetry or nephelometry, solid phase immune tests and 2D gel electrophoresis. If the position of the ADAM 12 protein (including its isoforms) in a 2D gel is known (e.g. identifiable by mass spectroscopy), then 2D gel electrophoresis may allow detection of ADAM 12 without use of a specifically binding ligand.

Other methods for measurement without use of a specifically binding ligand include different types of mass spectrometry, e.g. capillary electrophoresis mass spectrometry (CE-MS), surface enhanced laser desorption—time of flight (SELDI-TOF) mass spectrometry and the like (see e.g. Smith, R. (2002). Trends in mass spectrometry instrumentation for proteomics, Trends in Biotechnology, vol. 20, no. 12 (suppl.), pp. S3-S7).

In another preferred embodiment, the peptide or polypeptide has a sequence which is selected from the sequence presented in SEQ ID NO: 8.

This embodiment relates to the isoform ADAM 12-S. ADAM 12-S is soluble and can be found at high concentrations in the blood. Therefore, ADAM 12-S can be measured easily using ligands binding to a peptide or polypeptide with a sequence according to SEQ ID NO: 4 and 8, particularly SEQ ID NO: 8. For specific detection of the short isoform (ADAM 12-S) or the long isoform (ADAM 12-L), binding of the ligand should be determined by regions unique to these isoforms, such as the C-terminal ends of ADAM 12-L (SEQ ID NO: 6) and ADAM 12-S (SEQ ID NO: 8). An example is an antibody raised against such a peptide or polypeptide. A suitable antibody has been described previously (Gilpin, B. J., Loechel, F., et al. (1998). A Novel, Secreted Form of Human ADAM 12 (Meltrin a) Provokes Myogenesis in Vivo. Journal of Biological Chemistry 273(1), 157-166). Said antibody is directed against a region (encoded by base pairs 2000-2433 according to FIG. 1 of Gilpin et al., 1998, cited above), which contains the first 4 amino acids (EARA) of the C-terminal end unique to ADAM 12-S. However, in some samples, such as blood, ADAM 12-S is the most prevalent isoform and can be measured with a ligand directed against a region common to both isoforms.

In another preferred embodiment, the ligand is selected from the group consisting of
a) KB-R7785 or a derivative thereof;
b) TIMP-1, TIMP-3, IGFBP-3, IGFBP-5, HB-EGF, $\alpha_2$-macroglobulin, PKC-$\delta$, $\alpha$-actinin-1, $\alpha$-actinin-2, src, Grb-2, or syndecan-4;
c) antibodies;
d) nucleic acid or protein aptamers;
e) fragments or derivatives of any of the substances defined in b), c), or d).

Several ligands binding to ADAM 12 are known in the art, including small molecules (KB-R7785 (Asakura, M., Kitakaze, M., Takashima, S., Liao, Y. (2002). Cardiac hypertrophy is inhibited by antagonism of ADAM12 processing of HB-EGF: Metalloproteinase inhibitors as a new therapy. Nature Medicine 8: 35-40), polypeptides or proteins (TIMP-3, IGFBP-3, IGFBP-5, HB-EGF, $\alpha_2$-macroglobulin), and antibodies (see also Gilpin, B. J., et al. (1998), cited above). A polyclonal antibody against ADAM 12 is commercially available from Serotec (Cat. No. AHP758). Another antibody, directed against the pro-domain of ADAM-12, is available from Biomol (Cat. No. SA-378). The pro-domain is a domain that is cleaved off during activation of ADAM-12. Methods to generate antibodies or aptamers are well-known in the art. Identification and production of suitable antibodies or aptamers is also offered by commercial suppliers.

Notably, HB-EGF and IGFBPs, such as IGFBP-3 and IGFBP-5, are not only ligands of ADAM 12, but also substrates of the ADAM 12 proteolytic activity.

The person skilled in the art is familiar with methods to develop derivatives of the ligands according to a) to d) with higher affinity or specificity. For example, random mutations can be introduced into the proteins or substitutions into other molecules. These derivatives can then be tested for binding according to the screening procedure described above.

The term "antibody" as used herein includes both polyclonal and monoclonal antibodies, as well as fragments thereof, such as Fv, Fab and F(ab)$_2$ fragments that are capable of binding antigen or hapten. The present invention also includes "humanized" hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art.

In a preferred embodiment, the ligand is directed against a fragment of any of the substances defined in b), c), or d). It is well-known that binding of antibodies, nucleic acids, peptides, or polypeptides occurs via specific binding regions, so-called binding sites, epitopes, or binding pockets. Such binding regions can be determined by methods known in the art, e.g. mutational analysis or NMR spectroscopy. Thus, fragments including only said binding regions can be determined. Those fragments may bind similarly or better than the original antibody, nucleic acid, peptide, polypeptide. Such fragments can also be used according to the present invention.

In a preferred embodiment, the above described use of expression level(s), of nucleic acid molecules or ligands for diagnosis is done in conjunction with a diagnostic agent for the measurement of expression of any of the genes or proteins selected from the group consisting of (a) EPAS-1/HIF-2a, (b) neurokinin B, (c) TIMP-1, (d) VEGFR-1, (e) VEGF, (f) IGFBP-1, (g) IGFBP-3, (h) matrix metalloproteinase-2, (i) leptin, (j) PAI-1, (k) IGF-1, (l) angiopoetin-2, (m) PlGF, (n) HLA-G, (o) HB-EGF, (p) TGFβ-3, (q) decorin, (r), MIFR-2, (s) LIM, (t) EBI3, and/or a diagnostic tool for the measurement of blood pressure or protein content of the urine. Comparative results for some of these genes are shown in Example 8 and FIG. 7.

Furthermore, diagnosis may be carried out in conjunction with measurement of the expression level of one or more of the genes, peptides or polypeptides selected from those indicated in Table I in example 16 or those indicated in FIG. 6. Said Table I and FIG. 6 disclose further genes and peptides or polypeptides useful in the context of diagnosis of preeclampsia and related syndromes. Also described is their relative induction or repression of expression during preeclampsia. Several of the genes and proteins have not been previously disclosed as markers whose expression level is indicative of preeclampsia or a related syndrome.

The use of the expression level of the genes and proteins disclosed in Table I or FIG. 6, alone (e.g. without use of the expression level of ADAM-12) or in combination, as well as the use of corresponding nucleic acids and ligands are subject of the present invention. All embodiments of the present invention which relate to diagnosis of preeclampsia and related syndromes apply analogously to such genes, peptides and polypeptides.

Genes, peptides and polypeptides (and their corresponding expression level(s), nucleic acids, or ligands) selected from the group in Table I or FIG. 6 may be used alone or in conjunction with other diagnostic agents or tools for diagnosis of preeclampsia. Said genes, peptides or polypeptides (and their corresponding expression level(s), nucleic acids, or ligands) may also be used in conjunction with the expression levels(s), nucleic acids, or ligands of any other genes and proteins selected from Table I or FIG. 6.

Preferably, the combinations of at least two, more preferably at least 3, more preferably at least five, even more preferably at least eight, genes, peptides, or polypeptides selected from Table I or FIG. 6 are used.

Measurement of the expression level of more than one gene or protein generally holds the advantage of raising the specificity as well as the selectivity of diagnosis.

The person skilled in the art is able to determine of suitable combinations, e.g. according to the degree of induction or repression during preeclampsia or a related syndrome. Generally, combinations relating to genes showing strong induction or repression are preferred.

Preferred combinations may comprise (1) genes, peptides or polypeptides with more than three-fold, preferably more than 5-fold, more preferably more than 7-fold induction or repression according to Table I, or (2) genes according to Table I whose expression products are secreted and can be measured in a body fluid sample, preferably blood or blood serum, or (3) genes, peptides or polypeptides representing different biochemical functions or pathways, e.g. genes or proteins selected from the different groups A to F depicted in Table I, or (4) genes, peptides or polypeptides from little or non-related gene families, or (5) combinations of genes whose expression levels are induced (as opposed to repressed) during preeclampsia according to Table I. Preferably, the combinations fulfil at least two, preferably at least 3 of these selection criteria.

The person skilled in the art is able to determine if an expression product is secreted or not. Typical secreted expression molecules include secreted proteases (such as ADAM 12-S) or inhibitors thereof (such as TIMPs), secreted signaling molecules or shedded cell surface molecules (such as HB-EGF), and secreted cell matrix proteins (e.g. keratins). Examples are also provided by Mizutani, S., Akiyama, H., Kurauchi, O. et al. (1985) Plasma angiotensin I and serum placental leucine aminopeptidase (P-LAP) in pre-eclampsia. Arch. Gynecol. 236(3):165-72) and by Tempfer, C. B., Bancher-Todesca, D., Zeisler, H., et al. (2000) Placental expression and serum concentrations of cytokeratin 19 in preeclampsia. Obstet. Gynecol. 95(5):677-82).

Guidance and information concerning the properties and functions of the genes and their corresponding expression products can derived from public databases such as the Online Mendelian Inheritance in Man (OMIM) database, which is maintained at the United States National Library of Medicine at the National Institutes of Health, Bethesda, Md.).

A few non-limiting examples for combinations include:
1) ADAM 12-S combined with keratin 4 (X07695), and/or keratin 19 (Y00503)
2) ADAM 12-S combined with Epstein-Barr virus latent induced (EBI3, Acc. No. L08187)
3) HB-EGF combined with keratin 4
4) MIFR-2 (AB010962) combined with keratin 4
5) PlGF and/or EPO combined with TIMP-1 and/or TIMP/2
6) ADAM-12 combined with CD71 receptor (X01060)

Suitable diagnostic agents for the measurement of expression of said genes or proteins are known to the person skilled in the art. Suitable diagnostic agents can be defined analogously as above for ADAM 12. In particular, suitable diagnostic agents may comprise nucleic acids hybridizing to said genes or transcripts, antibodies, aptamers, and other ligands binding specifically to said proteins or the nucleic acids encoding said proteins.

Suitable antibodies are commercially available for most of the above defined proteins and can be found through public databases known to person skilled in the art, e.g. www.biocompare.com. Examples for suppliers are given in the following: EPAS-1/HIF-2α (Abcam, Novus-Biologicals), neurokinin B (United States Biological), TIMP-1 (Affinity BioReagents (ABR)), VEGFR-1 (Chemicon, Lab Vision, Upstate, CalTag), VEGF (Anogen, Assay Designs Inc., BD Biosciences Pharmingen, Chemicon, Novus Biologicals, and others), IGFBP-1 (Cell Sciences, Novus Biologicals), IGFBP-3 (BD Biosciences Pharmingen, Novus Biologicals), matrix metalloproteinase-2 (Affinity BioReagents (ABR), Chemicon, Lab Vision), leptin (Affinity BioReagents (ABR), BD Pharmingen, BioSource International, Chemicon, Peprotech, and others), IGF-1 (Novus Biologicals), PAI-1 (BD Biosciences Pharmingen, United States Biological), angiopoetin-2 (Chemicon, Zymed), PlGF (Cell Sciences), HLA-G (Novus Biologicals, Serotec Inc.), HB-EGF (R&D Systems), TGFβ-3 (Genex Bioscience), decorin (United States Biological).

Diagnostic tools for the measurement of blood pressure or protein content of the urine are known to the person skilled in the art. For example, the protein content of the urine may be measured by dip sticks.

In another preferred embodiment, a nucleic acid as defined above, a ligand as defined above, or, additionally, a diagnostic agent as defined above is present on an array.

Said array contains at least two nucleic acids as defined above, or ligands as defined above, or, additionally, diagnostic agents.

According to the present invention, the term "array" refers to a solid-phase or gel-like carrier upon which at least two compounds are attached or bound in one-, two- or three-dimensional arrangement. Such arrays are generally known to the person skilled in the art and typically generated on glass microscope slides, specially coated glass slides such as polycation-, nitrocellulose- or biotin-coated slides, cover slips, and membranes such as, for example, membranes based on nitrocellulose or nylon.

The aforementioned array may include a bound ligand, an above-defined nucleic acid, or at least two cells expressing at least one ligand or above-defined nucleic acid. In addition, said arrays may include a diagnostic agent or at least two cells expressing such diagnostic agent. Such arrays can be employed for diagnosis of preeclampsia and related syndromes.

The invention further relates to a method of producing arrays as defined above, wherein at least one above defined nucleic acid or ligand is bound to the carrier material in addition to other nucleic acids, ligands, or, additionally, diagnostic agents. Preferably, diagnostic agents for at least five, more preferably at least eight, additional marker genes or proteins are additionally bound to the carrier material.

Methods of producing such arrays, for example based on solid-phase chemistry and photo-labile protective groups, are generally known (U.S. Pat. No. 5,744,305). Such arrays can also be brought into contact with substances or substance libraries and tested for interaction, for example for binding or change of confirmation. Therefore, arrays comprising a peptide or polypeptide as defined above may be used for identifying ligands binding specifically to said peptides or polypeptides.

The invention further relates to a method for preparing an array immobilized on a support material for diagnosis of preeclampsia or a related syndrome, in which at least two nucleic acids, at least two polypeptides or at least two antibodies or antibody fragments, and/or at least two cells or at least one of the aforementioned components in combination with other components relevant to preeclampsia and related disorders are used for preparation. The arrays produced by such a method can be employed for diagnosis of preeclampsia or a related syndrome.

In another preferred embodiment, diagnosis relates to the diagnosis of syndromes related to preeclampsia.

According to the present invention, syndromes "related" to preeclampsia include other pregnancy-associated disorders or syndromes with similar aetiology and/or symptoms as preeclampsia. Particularly included are eclampsia, intrauterine growth retardation, "missed abortion", superimposed gestosis, and HELLP syndrome.

In another embodiment, the present invention also relates to a method of diagnosis in which the above defined nucleic acid molecules, ligands, or, additionally, diagnostic agents or tools are used.

Using the above-defined nucleic acid molecules or the above-defined peptides or polypeptides, it is possible to identify suitable ligands by methods known in the art.

Therefore, the present invention also relates to the use of any of the nucleic acid molecules as defined above or the use of peptides or polypeptides comprising peptides or polypeptides as defined above for the identification of ligands binding specifically to said nucleic acids, peptides or polypeptides.

Suitable methods may comprise the steps of binding ADAM 12 polypeptides or suitable fragments thereof (such as the isoform-specific C-termini) or a candidate for a ligand to a solid phase, contacting the polypeptide with the ligand and detecting the binding of the ligand to the polypeptide. Examples comprise affinity chromatography, yeast-two-hybrid screens and enzyme-linked immuno-sorbent assays (ELISA). Identification of suitable ligands is also offered by commercial suppliers (e.g. Graffinity, Heidelberg), including the identification of binding antibodies, aptamers, and small molecules.

Therefore, the present invention also relates to a method for the identification of ligands binding specifically to any of the peptides or polypeptides as defined above, comprising the steps of contacting the polypeptide with at least one candidate for a ligand, and measuring the binding of the candidate for a ligand to the polypeptide. Said method may further comprise the steps of providing the polypeptide and providing at least one candidate for a ligand. Said peptides or polypeptides may be provided by organic synthesis or recombinant expression using the nucleic acid molecules as defined above. The peptides or polypeptides may also be isolated or purified from body fluids or tissue from the dead or alive human or animal body. Suitable purification methods are well known in the art and include salt fractionation, size exclusion chromatography, ion exchange chromotography, reverse phase chromatography, and affinity chromatography (with or without help of suitable tags, such as His-tags and the like). The isolated or purified peptides or polypeptides may contain modifications, such as glycosylation, against which a suitable ligand or candidate for a ligand may be directed.

After contacting the polypeptide with the candidate for a ligand, one or more optional steps of washing can be included.

The method can be carried out in the solid phase or in the liquid phase. If the method is carried out in the solid phase it may comprise a step of binding the polypeptide or a fragment thereof or the test substance to a solid phase. However, the step of contacting the polypeptide with at least one candidate for a ligand may still be carried out in a liquid, particularly in an aqueous solution. Examples for such methods are affinity chromatography and enzyme-linked immuno-sorbent assays (ELISA).

In another preferred embodiment, the method may be carried out in the liquid phase. Examples for such methods may include UV-crosslinking, immunoprecipitation, nuclear magnetic resonance spectroscopy (NMR, also available commercially, e.g. by Combinature Biopharm).

In another preferred embodiment, a method for identification of ligands may comprise the steps of (a) coupling a peptide or polypeptide comprising a peptide or polypeptide as defined above with a further detection moiety, (b) coupling the candidate for a ligand with a second detection moiety that is capable of interacting with the first detection moiety, (c) contacting the polypeptide of step (a) with the candidate for a ligand of step (b), preferably in a liquid, more preferably an aqueous solution, (d) measuring the interaction of the detection moieties and thereby detecting the binding of the candidate for a ligand to the polypeptide.

An aqueous solution according to the present invention also relates to a cytosolic solution. Examples for such methods include fluorescent resonance energy transfer (FRET) and yeast-two-hybrid screens. The interaction between the detection moieties may be either covalent or non-covalent, preferably non-covalent. Examples for suitable detection moieties include fluorescent molecules, such as green fluorescent protein (GFP) and its derivatives (Miyawaki, A., Tsien, R. Y., Monitoring protein conformations and interactions by fluorescence resonance energy transfer between mutants of green fluorescent protein. Methods Enzymol. 2000; vol. 327, pp. 472-500) and transcription factors such as Gal4 and VP-16. Another optional step for a method of identification of ligands may comprise the step of comparing the binding of the candidate for a ligand to a related polypeptide, i.e. to another ADAM, such as ADAM 19, ADAM 33, or ADAM 2, to determine the specificity of binding.

In another embodiment, the present invention relates to a method for diagnosis of preeclampsia or a related syndrome comprising the steps of (a) bringing a tissue sample or body fluid sample in contact with a nucleic acid as defined above or a specifically binding ligand as defined above, and (b) detecting the binding of the nucleic acid or ligand. Preferably, the method is carried out in vitro.

Optionally, the method may include a step of obtaining a tissue sample or body fluid sample. Another optional step includes isolating nucleic acids or proteins contained in the sample.

In another embodiment, the present invention relates to the use of a nucleic acid as defined above, a ligand as defined above, optionally in combination with a diagnostic agent or diagnostic tool as defined above, for the manufacture of a diagnostic for the diagnosis of preeclampsia or a related syndrome.

In another embodiment, the present invention relates to a diagnostic containing a nucleic acid molecule, ligand, or, additionally, diagnostic agent as defined above. Such a diagnostic may be used for the diagnosis of preeclampsia or a related syndrome. The nucleic acid molecule, ligand, or, additionally, diagnostic agent in the diagnostic may be labeled or unlabeled. The nucleic acid, ligand or diagnostic agent may also be present on a suitable carrier, e.g. a dipstick.

In another embodiment, the present invention relates to a diagnostic kit containing a nucleic acid molecule, ligand, or, additionally, diagnostic agent and/or diagnostic tool as defined above. Such a diagnostic kit may be used for the diagnosis of preeclampsia or a related syndrome.

The nucleic acid molecule, ligand, or, additionally, diagnostic agent in the kit may be labeled or unlabeled. Additionally, the kit may contain specifically binding secondary or higher order ligands (e.g. antibodies) and auxiliary reagents and tools as appropriate and known in the art. Furthermore, the kit may contain control reagents, such as agents for measuring total RNA, total protein content, or the expression level of "housekeeping" genes or proteins, such as EF-1α, β-tubulin, cyclophilin B, HPRT, GAPDH, and others. The assays to be performed with the kit may be liquid phase assays as well as solid phase assays (i.e. with one or more reagents immobilized on a support). The kit may also comprise suitable tools for obtaining tissue or body fluid samples, particularly blood samples.

In another embodiment, the present invention also relates to a diagnostic or a diagnostic kit, wherein said nucleic acid, ligand or, additionally, diagnostic agent is present on an array. Preferably, diagnostic agents for at least five, more preferably at least eight, additional marker genes or proteins are additionally bound to the carrier material.

In another aspect, the invention relates to a method for the preparation of a diagnostic or a diagnostic kit, wherein a ligand of the peptides or polypeptides as defined above is identified according to the methods as defined above, synthesized in adequate amounts, and formulated into the diagnostic or diagnostic kit.

Similarly, said ligand may provided by any of the methods described above and formulated into the diagnostic or diagnostic kit.

The term "adequate amounts" of the ligand relates to any amounts sufficient for detection and/or measurement of said peptides or polypeptides. Suitable amounts depend on the particular method of detection or measurement, and are known to the person skilled in the art.

With respect to treatment, the problem according to the present invention is solved by use of a nucleic acid molecule comprising a nucleic acid selected from the group consisting of a) a nucleic acid with a sequence as presented in SEQ ID NO: 1 or 3;

b) a fragment of any of the nucleic acids as defined in a);

c) a nucleic acid with the antisense sequence of any of the sequences defined in a), or b);

d) single-stranded or double-stranded RNA with a sequence corresponding to any of the sequences defined in a), b), or c);

e) siRNA with a sequence defined in a), b), c), or d)

for the manufacture of a medicament for the treatment of preeclampsia or a related syndrome.

The problem is also solved by use of an inhibitor of the biological activity of a peptide or polypeptide with a sequence selected from the group consisting of a) an amino acid sequence as presented in SEQ ID No. 2 or 4;

b) an amino acid sequence exhibiting a sequence identity with any of the sequences according to a) of at least 85% over 100 residues;

c) a fragment of any of the sequences as defined above for the manufacture of a medicament for the treatment of preeclampsia or a related syndrome.

These nucleic acid molecules, nucleic acids, peptides, polypeptides and sequences are in the following included in the group of "above defined" nucleic acid molecules, nucleic acids, peptides, polypeptides or sequences.

Preferably, the nucleic acid molecules, nucleic acids, peptides, or polypeptides have been purified and/or isolated.

As a consequence of the present invention, it is known that upregulation of ADAM 12, particularly ADAM 12-S, plays a significant role in preeclampsia and related syndromes. Therefore, treatment by inhibiting expression or biological activity of ADAM 12, particularly ADAM 12-S, is an object of the present invention.

A particular advantage of the present invention is that inhibition does not have to be complete. Already a reduction of the biological activity of ADAM 12, preferably to near normal levels, can be sufficient for treatment. Thus, inhibition is also understood as a reduction of the biological activity of ADAM 12. Inhibition may also relate to modulation of ADAM 12 biological activity, such as modifying its substrate binding specificity or protease activity. It will be appreciated that inhibition of the biological activity can also be exerted through inhibition of expression, including inhibition of transcription, translation, or a decrease of transcript or protein stability.

According to the present invention, the term "inhibitor" relates to any substance inhibiting the biological activity of ADAM 12 or ADAM 12-S, particularly inhibiting the proteolytic or metalloproteolytic activity of ADAM 12 or ADAM 12-S. It also relates to inhibiting the binding of ADAM 12 or ADAM 12-S to endogenous substrates, such as HB-EGF or IGFBPs. It will be appreciated that all substrates of the proteolytic activity of ADAM 12 may be used as competitive inhibitors, including suitable peptides derived from those substrates. The person skilled in the art is familiar with identifying such peptides.

Preferably, the medicament is an inhibitor of expression or biological activity of ADAM 12 or ADAM 12-S. Inhibition of expression includes inhibition of transcription, translation, or a decrease of transcript or protein stability. Inhibition of biological activity particularly relates to inhibition of substrate binding activity or proteolytic activity.

A medicament according to the present invention preferably comprises additionally a suitable pharmaceutically acceptable carrier. The medicament may additionally comprise other carrier substances, preferably starch, lactose, fats, stearin acid, alcohol, physiological NaCl-solutions or further additives, in particular stabilizers, preservatives, dyes and flavourings. The medicament may also comprise other suitable substances. For example, an RNA or siRNA containing medicament may contain substances which stabilize RNA, particularly double-stranded RNA.

The above defined nucleic acid molecules are preferably used to inhibit expression of the corresponding endogenous genes. Nucleic acids which can be used to inhibit expression of the endogenous genes are known to the person skilled in the art. For example, peptide nucleic acids, comprising sequences as defined above, can suppress expression of the corresponding endogenous gene by forming DNA triplex structures with the gene. Other nucleic acids, such as antisense RNAs, siRNAs, morpholino oligonucleotides, or ribozymes, can be used to interfere with RNA transcribed from the endogenous gene. In particular, small interfering RNAs (siRNA) can be used for inhibition of expression of the endogenous gene.

In a preferred embodiment, the nucleic acids have sequences shown in SEQ ID NO: 1 or 3, which correspond to those presented in GenBank Acc. No. AF023476 or AF023477.

In another preferred embodiment, fragments of any of the nucleic acids as defined above are used, preferably fragments with sequences located in SEQ ID NO: 5 or SEQ ID NO: 7. Suitable fragments are known to the person skilled in the art. For example, suitable fragments may be a peptide nucleic acid or oligonucleotides or nucleic acid fragments encoding siRNAs (also described in Tuschl, Nature Biotechnology, Vol. 20, pp. 446-44).

In another preferred embodiment, said nucleic acids have the antisense sequence of any of the sequences defined above. Such nucleic acids may comprise peptide nucleic acids (PNAs), antisense morpholino oligonucleotides, or antisense or double-stranded RNAs. Therefore, in another preferred embodiment, said nucleic acids may be single-stranded or double-stranded RNA with sequences corresponding to any of the sequences defined above.

In another preferred embodiment, the above-defined nucleic acid is an siRNA with sequences as defined above.

The inhibition of a specific target gene in mammals is achieved by the introduction of an siRNA-molecule having a sequence that is specific for the target gene into the mammalian cell. The siRNAs comprise a first and a second RNA strand, both hybridized to each other, wherein the sequence of the first RNA strand is an oligonucleotide corresponding to one of the sequences as defined above for therapy and wherein the sequence of the second RNA strand is the antisense-strand of the first RNA strand. The siRNA-molecules may possess a characteristic 2- or 3-nucleotide 3'-overhang. Each strand of the siRNA molecule preferably has a length of 19 to 31 nucleotides.

The siRNAs can be introduced into the mammalian cell by any suitable known method of cell transfection, particularly lipofection, electroporation, or microinjection, be it in vitro or in vivo.

The RNA oligonucleotides can be generated and hybridized to each other in vitro or in vivo according to any of the known RNA synthesis methods, in order to obtain siRNA.

In another embodiment, the invention relates to the use of a nucleic acid molecule, wherein the nucleic acid molecule is contained in at least one nucleic acid expression vector which is capable of producing a double-stranded RNA-molecule comprising a sense-RNA-strand and an antisense-RNA-strand under suitable conditions, wherein each RNA-strand, independently from the other, has a length of 19 to 31 nucleotides.

In this alternative method (also described in Tuschl, Nature Biotechnology, Vol. 20, pp. 446-448), vector systems capable of producing siRNAs instead of the siRNAs themselves are introduced into the mammalian cell for downregulating gene expression.

In a preferred embodiment, the first and the second RNA strand of the siRNA may have, independently from the other, a length of 19 to 25 nucleotides, more preferred of 20 to 25 nucleotides, and most preferred of 20 to 22 nucleotides.

In another preferred embodiment, the first and the second RNA strand of the siRNA may have, independently from the other, a length of 26 to 30 nucleotides, more preferred of 26 to 28 nucleotides, and most preferred of 27 nucleotides.

In another embodiment, the present invention relates to a medicament comprising an above-defined nucleic acid molecule.

Administration of the medicament can be carried out by known methods. For therapeutic applications, the medicament may be in form of a solution, in particular an injectable solution, a cream, ointment, tablet, suspension, granulate or the like. The medicament may be administered in any suitable way, in particular by injection, by oral, nasal, rectal application. The medicament may particularly be administered parenteral, that means without entering the digestion apparatus, for example by subcutaneous injection. In particular, the medicament may also be injected intravenously in the form of solutions for infusions or injections. Other suitable administration forms may be direct administrations on the skin in the form of creams, ointments, sprays and other transdermal therapeutic substances or in the form of inhalative substances, such as nose sprays, aerosoles or in the form of microcapsules or implantates.

Preferably, the inhibitor is administered in pharmaceutically effective amount. As used herein, a "pharmaceutically effective amount" of an inhibitor is an amount effective to achieve the desired physiological result, either in cells treated in vitro or in a subject treated in vivo. Specifically, a pharmaceutically effective amount is an amount sufficient to positively influence, for some period of time, one or more clinically defined pathological effects or symptoms associated with preeclampsia. The pharmaceutically effective amount may vary depending on the specific inhibitor selected, and is also dependent on a variety of factors and conditions related to the subject to be treated and the severity of the disorder or symptom. For example, if the inhibitor is to be administered in vivo, factors such as age, weight, gestational age, and general health of the patient as well as dose response curves and toxicity data obtained in pre-clinical animal tests would be among the factors to be considered. If the inhibitor is to be contacted with cells in vitro, one would also design a variety of pre-clinical in vitro studies to asses parameters like uptake, half-life, dose, toxicity etc. The determination of a pharmaceutically effective amount for a given agent is well within the ability of those skilled in the art. Preferably, the inhibitor is present in a concentration of 0.1 to 50% per weight of the pharmaceutical composition, more preferably 10 to 30%.

In another embodiment, the present invention relates to a method of treatment of preeclampsia or a related syndrome comprising the use of the above-identified nucleic acid molecules.

Treatment of preeclampsia or a related syndrome relates to treatment of the disorder or syndrome itself as well as treatment of symptoms associated with said disease or syndrome. Such symptoms may include intravascular coagulation, blood platelet destruction, high blood pressure, edema, proteinuria, or placental abruption. Treatment according to the present invention also relates to prophylaxis.

Treatment according to the present invention may be accompanied by treatment approaches known in the art, for example blood pressure control (particularly by administration of alpha-receptor blockers (e.g. hydralazine) or ebrantil), tocolysis (particularly for increase of placental blood flow), administration of magnesium, and administration of cortisone.

In another preferred embodiment, the inhibitor is a disintegrin domain metalloproteinase inhibitor, particularly KB-R7785, a TIMP, particularly TIMP-3 or a fragment thereof, $\alpha_2$-macroglobulin, or an antibody directed against ADAM 12.

In a preferred embodiment, such an inhibiting antibody is directed against the proteolytic domain of ADAM 12, particularly the zink binding domain, more particularly including amino acid positions 350-361.

Preferably, the inhibitor should be specific for ADAM 12, ADAM 12-L, or ADAM 12-S. The criteria for specificity as defined above for ligands apply analogously.

In a preferred embodiment, the peptide or polypeptide is a fragment with a sequence consisting of or located in SEQ ID NO: 8. According to this embodiment, the inhibitor is directed specifically against a peptide or polypeptide consisting of or located in SEQ ID NO: 8. An example is an antibody raised against such a peptide or polypeptide. It is known that such antibodies, though in this case binding only to the C-terminus of ADAM 12-S, can sterically inhibit the biological activity of the entire ADAM 12-S protein. The same is true for aptamers and other inhibitors. Suitable inhibitors can be found by identifying ligands binding specifically to ADAM 12-S and subsequently screening them as candidates for inhibitors. Analogously, inhibitors directed against the C-terminus of ADAM 12-L (SEQ ID NO: 6) may be identified.

In another preferred embodiment, the above-defined nucleic acid or inhibitor is used in conjunction with HB-EGF. Preferably, HB-EGF has been purified or isolated. Preferably, HB-EGF is formulated into the medicament defined above.

In another preferred embodiment, the medicament is for treatment of symptoms of preeclampsia or a related syndrome, particularly for treatment or prevention of intravascular coagulation, blood platelet destruction, high blood pressure, edema, glomerular endotheliosis, proteinuria, or placental abruption.

Symptoms of preeclampsia and related syndromes include any undesired effects the disorders may have on the mother or fetus. Particularly, symptoms relate to symptoms caused by a high level of ADAM 12 in the blood, particularly the maternal blood. More particularly, such symptoms include intravascular coagulation (thrombosis), blood platelet destruction, or high blood pressure (particularly above 140/90 mm Hg), edema (swelling of face and/or hands), glomerular endotheliosis, or proteinuria (particularly more than 0.3 g/24 hours or a level of 2+ by dipstick test).

Treatment may also be restricted to the mother's blood. For example, IgM antibodies or other molecules of high molecular weight have only a limited capability of passing the placental blood barrier. Therefore, in a preferred embodiment, the inhibitor may be an IgM or any other molecule not capable of passing the placental blood barrier, particularly being of similar or higher molecular weight as an IgM. For example, an identified inhibitor, such as an aptamer, may be coupled covalently or non-covalently to a high molecular weight residue, such as a polypeptide or dextran.

In another aspect, the present invention relates to the use of the nucleic acids, peptides or polypeptides as defined above for identification of inhibitors of the biological activity of the above-defined nucleic acids, peptides or polypeptides, particularly for identification of inhibitors of the proteolytic activity or substrate-binding activity of such peptides or polypeptides.

The person skilled in the art is familiar with such use of nucleic acids, peptides or polypeptides. Examples for suitable methods are described in the following.

Therefore, in another aspect, the present invention relates to a method for identification of inhibitors of any of the peptides or polypeptides as defined above, comprising the steps of (a) contacting said peptide or polypeptide with a suitable substrate, e.g. HB-EGF, (b) measuring the decrease in processing of the substrate in the presence as compared to the absence of a candidate for an inhibitor molecule.

Suitable substrates include all substrates of biological, preferably enzymatic, more preferably proteolytic activity. Suitable substrates include HB-EGF and IGFBPs, particularly IGFBP-3 and IGFBP-5. Processing of the substrate relates preferably to enzymatic modification, more preferably proteolytic modification or cleavage of the substrate. Measurement of processing can be done e.g. by measuring the decrease in substrate (educt) and the increase in modified substrate (product). Measurement of processing can involve indirect measurement, e.g. via ligands, labeled or unlabeled (see above) binding to the substrate or modified substrate.

Candidates for inhibitor molecules can be any nucleic acid, peptide, polypeptide or other substance. In particular, candidates may include peptides derived from TIMP, IGFBP-3, IGFBP-5, HB-EGF, $\alpha_2$-macroglobulin, antibodies, nucleic acid or protein aptamers or fragments or derivatives of any of these substances. Other candidates for inhibitor molecules may comprise derivatives of KB-R7785. The person skilled in the art is familiar with methods of generating such derivatives, either by methods of combinatorial chemistry or introducing mutations into the respective nucleic acids or polypeptides.

In a preferred embodiment, the present invention relates to the candidate for inhibitor being a substrate or ligand as defined above. Any substrate of ADAM 12 or ADAM 12-S or ligand as defined above is also considered a candidate for an inhibitor.

In another aspect, the present invention relates to a method for the preparation of a pharmaceutical composition, wherein an inhibitor of the nucleic acids, peptides or polypeptides as defined above is identified according to the method as defined above, synthesized in adequate amounts, and formulated into a pharmaceutical composition.

Suitable methods to synthesize the inhibitor molecules are known in the art. For example, peptides or polypeptides can be synthesized by recombinant expression (see also above), and antibodies can be obtained from hybridoma cell lines or immunized animals. Small molecules can be synthesized according to any known organic synthesis method.

Similarly, said inhibitor may be provided by any of the screening methods described above and formulated into a pharmaceutical composition.

The term "adequate amounts" of the inhibitor relates to any amounts sufficient for inhibiting expression or biological activity of ADAM-12 in the human or animal body, preferably the human body. In particular, adequate amounts relate to pharmaceutically effective amounts.

DESCRIPTION OF THE FIGURES

FIG. 4 Increased ADAM-12 mRNA levels in preeclamptic human placenta. In situ detection of ADAM-12 transcripts in sections of placentae from gestational age-matched women with preterm labour (control, ctrl.) or preeclampsia (preecl.). Numbers indicate the gestational age when placenta tissue was taken. In the control placentas ADAM 12 transcripts are predominately localized to the syncytial knots of the placental villi indicated by arrows. By contrast, in preeclamptic placentas, ADAM 12 mRNA levels are increased and transcripts are additionally seen in the complete syncytiotrophoblast layer, indicated by arrow heads.

FIG. 5 Lower magnifications of the same tissue sections as shown in FIG. 4, as well as additional samples from preeclamptic placentae.

FIG. 6 Identification of genes deregulated in preeclamptic placentas by microarray analysis and classification of the 91 most regulated genes under conditions of preeclampsia during gestation. Independent sets of hybridizations addressed the gene expression profiles of different gestational age-matched patient pairs (concerning the six investigated patient pairs see table in example 8). Shown are results from 5 patient pairs. Placental tissue samples taken from the fetal (f) or maternal (m) side were analysed independently. All hybridizations were performed in duplicate including a colour switch. The 91 genes are induced or repressed by more than 2.5-fold in their expression levels during gestation. Genes were grouped into groups A to F according to functional classification and subjected to hierarchical tree clustering. The signal strength in the classification scheme is shown in a gray scale code, in which induced genes are indicated by darker shades and repressed genes by lighter shades. A, cell and tissue structural dynamics; B, metabolism; C, regulation of gene expression, D, intercellular communication; E, cell cycle and apoptosis; F, proteinases and inhibitors.

FIG. 7 Validation of microarray results by RT-PCR. (A) Semi-quantitative RT-PCR analysis of RNA from different gestational weeks of healthy (ctrl.) or preeclamptic (preecl.) placentas, as indicated, confirmed differential expression for an initial set of 4 most regulated genes: ADAM 12-S, EBI, MIFR-2, LIM-Hox. For LIM-Hox nested PCR was performed as documented in Example 9. (B) Quantitative Real Time RT-PCR analysis for ADAM 12-S mRNA levels from different gestational age-matched tissue samples taken from the fetal side of healthy or preeclamptic placentas. Cyclophilin B was used for normalization. Primer pairs used for PCR analysis are listed in Example 9 and 15. Relative ADAM 12 expression level (x-upreg.) was calculated by normalizing the amount of ADAM 12 transcript measured for preeclamptic placentas to that obtained from gestational age-matched healthy placentas that was set to a value of 1. Box plots are shown, which mark the interval between the $25^{th}$ and $75^{th}$ percentiles. The whiskers denote the interval between the $5^{th}$ and $95^{th}$ percentiles. The solid line within the boxes or the thick one on the edge indicates the median, the dotted line stands for the mean. The filled circles mark the data points outside the $10^{th}$ and $90^{th}$ percentiles. GA, gestational age; f, fetal side of placenta; m, maternal side of placenta.

Figure 1:
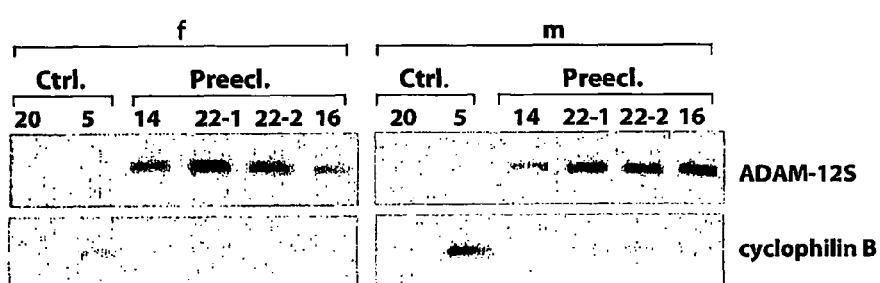
FIG. 1 Increased ADAM 12-S expression in preeclamptic human placenta. A, gestational age (GA, weeks+days) of the study subjects (Pat. No.). B, Semi-quantitative RT-PCR analysis for the levels of ADAM 12-S transcripts in human placenta using cyclophilin B for normalization. Note the increased level of ADAM 12-S transcript in samples of preeclamptic patients (Preecl.) as compared samples of healthy mothers (Ctrl.). The increase is visible both in the fetal (f) and maternal (m) part of the placenta. Patient 22 was pregnant with twins, and samples 22-1 and 22-2 were derived from the placentae belonging to each of the twins. The patient numbers in this figure do not correspond to patient numbers in FIG. 8.

The invention is further illustrated by the following examples, which are not intended to limit the scope of the invention in any way.

EXAMPLE 1

Placentae from different gestational age from preeclamptic patients as well as from healthy control patients were dissected and collected within less than 15 min after delivery. 10-20 mm thick sections were dissected and the fetal and maternal side were collected separately. Tissue was either immediately snap frozen or fixed in 4% paraformaldehyde for 12 hours. The fixed tissue was washed twice in phosphate-buffered saline (PBS, composition of 1 l: 8 g NaCl (137 mM), 0.2 g KCl (2.7 mM), 1.44 g $Na_2HPO_4.2H_2O$ (8.1 mM), 0.24 g $KH_2PO_4$ (1.76 mM), pH 7.4), transferred to 70% ethanol and paraffin embedded. For RNA preparation the tissue was incubated for 24 hrs in RNALater (Ambion) at 4° C. and then frozen and kept at −80° C. until use.

Patients characteristics. Samples were obtained form pregnant women at the Department of Obstetrics and Gynaecology, University Hospital Heidelberg. The study was approved by the Local Ethics Committee. Two groups of women were studied: control (healthy) pregnancies with no hypertension and women with pregnancies complicated by preeclampsia. 17 patients were enrolled into the study. Pairs of control and preeclamptic patients were matched according to their gestational age. For maternal reproductive data and delivery characteristics see FIG. 8. Two patients were lost to follow-up. Preeclampsia was defined by blood pressures of 140/90 mmHg measured twice within an interval 6 h and proteinuria of 3+ or 300 mg in a 24 h urine collection in women who were normotensive before pregnancy and had no other underlying clinical problems such as renal disease. Intrauterine growth retardation was determined following the Hadlock criteria.

EXAMPLE 2

Total RNA was isolated from frozen placental tissue, either from healthy or preeclamptic pregnant women of different gestational age, with TRIzol (a mono-phasic solution of phenol and guanidine isothiocyanate, Invitrogen, Karlsruhe, Gemany) according to the manufacturer's recommendations. The integrity and purity of the total RNA was checked on a 1% agarose gel with denaturing loading buffer or on the RNA 6000 Nano Chip (Agilent Technology, Germany). Total RNA quality and concentration was determined by absorption spectroscopy between 220 and 320 nm (1 $OD^{260}$=40 µg/ml ssRNA).

EXAMPLE 3

The microarrays contained 1600 nonredundant, sequence-validated human cDNAs (RZPD set, Berlin, (Fritz, B., et al. (2002). Microarray-based copy number and expression profiling in dedifferentiated and pleomorphic liposarcoma. Cancer Res, vol. 62: 2993-8). The cDNAs had been selected on their putative involvement in tumorigenesis and were PCR amplified as described previously (Wrobel, G., et al. (2003). Optimization of high-density cDNA-microarray protocols by 'design of experiments'. Nucleic Acids Res, vol. 31: e67, and Schlingemann, J., et al. (2003). Profile of gene expression induced by the tumor promotor TPA in murine epithelial cells. Int J Cancer 104(6), p. 699-708), purified by isopropanol precipitation and dissolved in 20 µl FBNC (Formamid, betaine and nitrocellulose) spotting buffer (Wrobel, G., et al.

(2003), see above). The resulting cDNA fragments had an average length between 500-1500 bp.

EXAMPLE 4

DNA spotting was performed on Poly-Prep poly-L-lysine coated substrates (Sigma Chemical Co.; However, also other substrates known in the art may be used, such as QF Epoxy substrates (Quantifoil Microtools, Jena, Germany)) using an OmniGrid Microarrayer (GeneMachines, San Carlos, Calif.) equipped with Stealth SMP3 Micro Spotting Pins (Telechem). Spot centres were 250 µm apart. The arrays were provided with positive control spots of the Spot Report System (Stratagene, Amsterdam, The Netherlands) as well as a variety of additional negative controls, e.g., mouse Cot-1 DNA (Invitrogen), yeast tRNA (Sigma Chemical Co.) and poly-dA (Amersham Biosciences). Furthermore, Cy3- and Cy5-labeled DNA was included to yield specific fluorescent landmarks on the arrays. DNA immobilisation to the glass was achieved by 3.5 hours of incubation at 80° C., followed by 2× irradiation at 254 nm with an energy of 120 mJ/cm$^2$ in a Stratalinker Model 2400 UV illuminator (Stratagene).

EXAMPLE 5

Sample preparation: 30-40 µg of total RNA (as obtained according to Example 2) was used for microarray hybridisation. Reverse transcription was performed in accordance to Wrobel et al., 2003, using an Omniscript RT Kit (QIAGEN) and Cy3/Cy5-dUTPs (NEN Life Science Products, Köln, Germany). Subsequently, Cy3- and Cy5-labeled cDNA samples were pooled (age matched placental tissue from healthy and preeclamptic placental tissues), purified and concentrated to 10 µl using a Microcon YM-30 PCR filter unit (Millipore, Eschborn, Germany), as previously described.

EXAMPLE 6

Microarray hybridisation: 31 µl of DIG Easy Hybridisation buffer (Roche Diagnostics, Mannheim, Germany) were added to each cDNA pool and incubated for 15-60 min at room temperature. Denaturation was carried out at 65° C. for 3 min. Hybridisation was performed for 16 h at 37° C. in Arraylt Hybridisation cassettes (TeleChem International, Sunnyvale) in a waterbath. Thereafter the slides were washed at room temperature with (i) 1×SSC, 0.1% (w/v) SDS for 10 min for 3 times; (ii) 0.1×SSC, 0.1% SDS for 10 min; (iii) H$_2$O for 3 min; (iv) 70% ethanol for 3 min; (v) 90% ethanol for 3 min; (vi) 100% ethanol for 3 min and (vii) finally dried with compressed air.

EXAMPLE 7

Data acquisition, processing and analysis: Microarrays were scanned and analysed using a GenePix 4000A microarray scanner (Axon Instruments, Inc., Union City, N.J.), controlled by the software GenePix Pro 3.0 (Axon Instruments, Inc.). Individual data reports for all conducted experiments (including, e.g., median fluorescence intensities of all spots and local background) were exported and further analysed using the R software environment for statistical computing as well as Microsoft Excel 2000. Data sets for spots not recognized by the GenePix analysis Software were excluded from further considerations. Additionally, all remaining data sets were ranked according to spot homogeneity (as assayed by the ratio of median and mean fluorescence intensities), spot intensity and the standard deviation of log ratios for replicate spots. Those data points ranked among the lower 50%, and thus possessing the lower reliability based on the criteria just described, were eliminated. Data sets that could not be verified, either in a colour switch experiment (reversed assignment of fluorophores) or on a different experimental day, were omitted as well. For each hybridisation, fluorescence ratios (Cy5/Cy3) were normalized by variance stabilization (Huber, W., von Heydebreck, A., Sultmann, H., Poustka, A., and Vingron, M. 2002. Variance stabilization applied to microarray data calibration and to the quantification of differential expression. Bioinformatics, vol. 18, 96-104) or the median log ratio of all genes found in this experiment. In median log ratio normalization, accurate differential expression values for each gene were obtained by calculating the average of the normalized ratios of all independent hybridisations, successfully identifying that gene, and reversing the ratios from colour switch experiments prior to this operation.

EXAMPLE 8

Comparative microarray analyses were performed for with the microarray as described in Example 3. The following pairs of samples with the indicated gestational ages (gestational weeks+days) were used:

| Pair No. | healthy (control) | preeclamptic |
|---|---|---|
| 1 | 41 + 3 | 41 + 0 |
| 2 | 38 + 2 | 38 + 2 |
| 3 | 34 + 0 | 35 + 1 (1) |
| 4 | 34 + 0 | 35 + 1 (2) |
| 5 | 34 + 0 | 33 + 2 |
| 6 | 27 | 25 |

Figure 2:
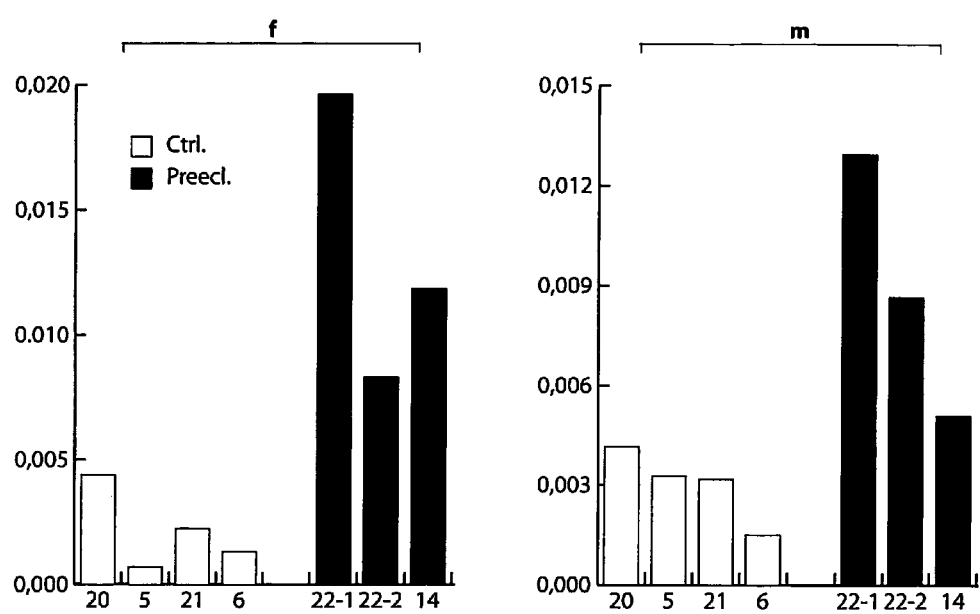
FIG. 2 Increased ADAM 12-S expression in preeclamptic human placenta. Shown are relative mRNA levels for ADAM 12-S in the fetal (f) or maternal (m) part of healthy (Ctrl.) and preeclamptic (Preecl.) human placentas as determined by real time PCR using elongation factor EF-1$\alpha$ for normalization. Note the increased level of mRNA in samples of preeclamptic patients as compared samples of healthy pregnant women. Y-axis: level of fluorescence of the PCR product (which is correlated with the level of mRNA in the sample), X-axis: Sample numbers, corresponding to the patient numbers (Pat No.) in FIG. 1A. Patient 22 was pregnant with twins, and samples 22-1 and 22-2 were derived from each placenta of twin siblings. The patient numbers in this figure correspond to the patient numbers indicated in FIG. 1.

35+1 (1) and 35+1 (2) designate samples derived from each placenta of twin siblings (patient 22, see legend to FIGS. 1 and 2).

Patient pair no. 5 was not included in the cluster analysis according to FIG. 6.

It was found that ADAM-12 was the most strongly regulated gene. Shown below are the data of Pair No. 2. Expression levels were calculated from two independent experiments. Calculation was performed using Microsoft Excel according to median log ratio normalization.

| Part of placenta | induced (upregulated) | | | repressed (downregulated) | | |
|---|---|---|---|---|---|---|
| | fetal | maternal | both | fetal | maternal | both |
| No. of genes induced more than 2-fold | 35 | 27 | 27 | 35 | 35 | 34 |
| ADAM-12 | 38-fold | 44.5-fold | — | — | | |
| TIMP-1 | 8.5-fold | 12-fold | — | — | | |
| TIMP-2 | 13-fold | 11.5-fold | — | — | | |
| EPAS/HIF-2α | 4-fold | 2.5-fold | — | — | | |

-continued

| Part of placenta | induced (upregulated) | | | repressed (downregulated) | | |
|---|---|---|---|---|---|---|
| | fetal | maternal | both | fetal | maternal | both |
| IGFBP-1 | — | — | | less than 2-fold | 7.5-fold | |
| IGFBP-3 | — | — | | 2.6-fold | 5.7-fold | |
| TEK | — | — | | 4.8-fold | 2.8-fold | |
| Decorin | — | — | | less than 2-fold | 6.5-fold | |

ADAM 6 and ADAM 9 were also included on the microarray, but were not found to be induced or repressed by more than 2-fold.

EXAMPLE 9

RT-PCR analysis. For RT-PCR analysis 2-5 µg total RNA from healthy and preeclamptic placental tissue of different gestational age pretreated with RQ1-DNase (Promega, Madison, Wis.) were reverse transcribed in a reaction volume of 20 µl using AMV-RT (Promega) and an oligo-d(T) (Promega) according to the manufacturer's recommendations, 2-3 µl of the RT reaction together with primers depicted in the following table were used for PCR detection.

| Primer Pairs used for RT-PCR analysis | | |
|---|---|---|
| Gene Name | Forward primer 5' | Reverse primer 3' |
| ADAM 12-L | CCTGTGACCTCCCAGAGTTCTGC (SEQ ID NO: 9) | GAATTCCTATGGTTAAACCTTGG (SEQ ID NO: 10) |
| ADAM 12-L | CTTGCTGCCGGATTTGTGGTTTAT (SEQ ID NO: 11) | AGTTGACTGGGGCTGAGGGACATT (SEQ ID NO: 12) |
| ADAM 12-S | CCTGTGACCTCCCAGAGTTCTGC (SEQ ID NO: 9) | GGACTCTGCAGCTTCCTGCCTTG (SEQ ID NO: 14) |
| ADAM 12-S | TCGGGGCTCAGGAGGGGAAGT (SEQ ID NO: 15) | GGCTGCCAAGGCGGAGGTGTC (SEQ ID NO: 16) |
| human cyclophilinB | GGCCGGGTGATCTTTGGTCTCTTC (SEQ ID NO: 17) | CCCGGCTGTCTGTCTTGGTGCTCT (SEQ ID NO: 18) |
| human EF-1α | CTGCTGAGATGGGAAAGGGCT (SEQ ID NO: 19) | TTCAGGATAATCACCTGAGCA (SEQ ID NO: 20) |
| EBI 3 | GAATTCCGCAGC-CATGACCC | GGGCTTGATGATGTGCTCTG |
| MIFR-2 | CAGCTGGAAGAAAGGCGT-GTG | GGGGGCGGTGGGGTGGTG |
| LIM (1st amplification) | AAGCGCATGCGCACGTCCTT | GGGTTGCGAGTCATTAG-AAAAGG |
| LIM (2nd amplification) | TTCAAGCACCACCAGCTTCGGA | AGAGTCGTTTGTGAGGGGCTGT |

Human cyclophilin B served as an internal control for the quality and quantity of the cDNA. Amplified probes of semi-quantitative RT-PCR were separated on 1.5% agarose gels in the presence of ethidium bromide and visualised by using the Eagle Eye system (Stratagene). To obtain a calibration graph for Real-Time PCR, cDNA PCR product from human elongation factor EF-1α was serially diluted in $H_2O$ (five 10-fold dilutions from 0.01 pg to 10 pg). To standardize the amount of sample cDNA, an endogenous control amplicon was used (EF-1α).

EXAMPLE 10

Semi-quantitative RT-PCR was performed on placental tissue samples obtained from 4 healthy and 3 preeclamptic patients (FIG. 1A). Typical results of the RT-PCR amplifications are shown in FIG. 1B. Samples 22-1 and 22-2 were obtained from the same patient.

A comparison of data from healthy (ctrl.) and preeclamptic women is shown in the graph of FIG. 2. Overall, the quantitative RT-PCR experiments demonstrate a 4 to 5-fold increase in ADAM 12-S transcript in placental tissue of both maternal and fetal origin.

EXAMPLE 11

The following procedure was used to obtain RNA from plasma samples. Peripheral blood samples were collected with informed consent of the patients. 5 to 10 ml blood samples were collected in EDTA-containing tubes and centrifuged at 4000 rpm for 15 min at 4° C. Plasma was collected in new tubes. The plasma samples were recentrifuged at 13000 rpm for 15 min at 4° C.

For analysis of RNA derived from plasma, the supernatants obtained in the above procedure are transferred to fresh tubes and can be processed according to a previously reported protocol, which is herewith incorporated by reference (Ng, E.K.O., Leung, T. N., et al. (2003). The concentration of circulating Corticotropin-releasing hormone RNA in maternal plasma is increased in preeclampsia. Clin. Chem. 49, 727-731, see particularly p. 728-729 and Ng, E.K.O., Tsui, N. B. Y., et al. (2003). Messenger RNA of placental origin is readily detectable in maternal plasma. Proc Natl Acad Sci USA, vol. 100(8):4748-53, see particularly p. 4748-4749).

EXAMPLE 12

For Real-time Quantitative PCR (RQ PCR), the QuantiTect' SYBR Green PCR Kit (Qiagen, Hilden, Germany) was used to amplify ADAM-12S specific templates from cDNAs of placental RNA of different patients according to the manufacturer's instructions. The amount of the amplified templates in each sample was analysed with the MJ Research Opticon™ (Biozym, Oldendorf, Germany) calculating against a standard PCR with elongation factor EF-1α, amplified from different dilutions.

Quantitative assessment of the DNA amplification was detected via the dye SYBR Green, the fluorescence of which is strongly enhanced upon the binding to the dsDNA. The RQ-PCR reactions were carried out in 50 µl using 1 µl of the RT reaction at a primer concentration of 0.3 µm, respectively, according to the manufacturer's recommandations for QuantiTect™ SYBR Green PCR Kit reagents (Qiagen, Hilden, Germany). The oligonucleotides used for real time PCR are listed in example 9. For thermal cycling the following conditions were applied: one step at 94° C. 15 min, then 40 cycles of 30 sec at 94° C., 1 min at 56° C. and 1:30 min at 72° C. and a final step at 72° C. for 3 min. Melting curve was achieved from 50 up to 93° C. within reading every 0.5° C. hold for 10 sec between reads to obtain melting curves of the final RQ-PCR products. This is necessary because SYBR Green fluorescence may also be derived from side products such as primer dimers.

To obtain a calibration graph, cDNA PCR product from elongation factor EF-1α was serially diluted in $H_2O$ (five 10-fold dilutions from 0.01 pg to 10 pg). To standardize the amount of sample cDNA, an endogenous control amplicon was used (EF-1α).

EXAMPLE 13

Sample preparation and Western Blot analysis of Patients sera. 5 to 10 ml blood samples were collected in EDTA-containing tubes and centrifuged at 4000 rpm for 15 min at 4° C. and supernatants were stored at −80° C. until use. For immunoblotting sera from normal and pre-eclamptic pregnancies were diluted 1:40 in PBS. 10 µl of the samples were denatured and reduced by boiling in SDS sample buffer containing dithiothreitol, followed by separation on 8% polyacrylamide gels. Transfer to nitrocellulose membranes was followed by blocking in TBST containing 5% BSA and 7% milk powder for 1 h at 4° C. Membranes were incubated with rabbit polyclonal anti-ADAM-12 serum at a dilution of 1:1000 in blocking buffer over night at 4° C. The anti-ADAM-12 antibody serum (rb122) was a kind gift from U. M. Wewer. The antibody was raised against the cysteine-rich domain of ADAM-12 and is equivalent to the rb104 antibody described in detail in Gilpin, B. J., Loechel, F., Mattei, M.-G., Engvall, E., Albrechtsen, R., and Wewer, U. M. (1998). A Novel, Secreted Form of human ADAM 12 (Meltrin alpha) Provokes Myogenesis in Vivo. J. Biol. Chem. 273, 157-166, see particularly page 158. The members were washed with blocking buffer incubated with peroxidase-conjugated goat anti-rabbit immunoglobulins (DakoCytomation) for 40 min at room temperature. Detection was performed using the Western lightning chemiluminescence kit from Perkin Elmer Life Sciences.

EXAMPLE 14

In situ hybridisation: In situ hybridisation was performed on 6 µm paraffin sections according to methods known in the art and described previously (Schorpp-Kistner M, Wang Z Q, Angel P, Wagner E F. JunB is essential for mammalian placentation. EMBO J. 1999 Feb. 15; 18(4):934-48. Gack S, Vallon R, Schmidt J, Grigoriadis A, Tuckermann J, Schenkel J, Weiher H, Wagner E F, Angel P. Expression of interstitial collagenase during skeletal development of the mouse is restricted to osteoblast-like cells and hypertrophic chondrocytes. Cell Growth Differ. 1995 June; 6(6):759-67). The antisense ADAM-12S cRNA probe was produced by in vitro transcription from an SalI linearized plasmid, containing a 677 by fragment (nt 1769-2445 of the published sequence: Acc. No. AF 023477).

EXAMPLE 15

For the experiments shown in FIG. 7, the following RQ-PCR protocol was used:

Quantitative differences in mRNA levels in healthy and preeclamptic placental samples were determined by real-time PCR and a thermal cycler controlled by the MyiQ Real Time Detection System software (BioRad, Munich, Germany). The Absolute SYBR Green Fluorescein Kit (ABgene, Surrey, UK) was used to amplify ADAM 12-S specific templates according to the manufacturer's instructions. The amount of the amplified ADAM 12-S templates in each sample was analysed calculating against a standard PCR with human cyclophilin B, amplified from different dilutions.

The sequences of the ADAM 12-S oligonucleotides used for real time PCR were SEQ ID NO: 15 and SEQ ID NO: 16 (see Example 9). For thermal cycling the following conditions were applied: one step at 95° C. 15 min, then 45 cycles of 30 sec at 95° C., 45 sec at 56° C. and 60 sec at 72° C., followed by a melting curve program (denaturation at 95° C.; cooling and holding at 60° C. for 10 s and heating at a speed of 0.5° C./10s to 100° C. with readings at every 0.5° C.). To obtain a calibration graph, cDNA PCR product from cyclophilin B was serially diluted in $H_2O$ (five 10-fold dilutions from 0.0001 ng to 1 ng). To standardize the amount of sample cDNA, an endogenous control amplicon was used.

EXAMPLE 16

Microarray analysis was used to compare gestational age-matched placental tissue from healthy and preeclamptic pregnant females (FIG. 8 and table in example 8) using a 1.6K human cDNA chip (Fritz, B., F. Schubert, G. Wrobel, C. Schwaenen, S. Wessendorf, M. Nessling, C. Korz, R. J. Rieker, K. Montgomery, R. Kucherlapati, G. Mechtersheimer, R. Eils, S. Joos, and P. Lichter. 2002. Microarray-based copy number and expression profiling in dedifferentiated and pleomorphic liposarcoma. Cancer Res 62:2993-2998). We performed separate microarray hybridizations using samples of the maternal and fetal part of the placentas from five gestational age-matched patient pairs. The samples represented ascending gestational weeks of the third trimester (27/25, 34/35(1), 34/35(2), 38/38 and preterm 41/41; see table in Example 8). Of 1600 genes represented on the chip, 91 genes were significantly altered in their expression levels by ≧2.5-fold in preeclamptic placental tissue. Among these genes, 74 were found to be up- and 17 downregulated in preeclamptic samples. The differentially expressed genes could be assigned to 6 functional subsets: cell and tissue structural dynamics (21 fetal/22 maternal genes), metabolism (18/18), regulation of gene expression (20/20 genes), intercellular communication (21/21 genes), cell cycle and apoptosis (5/5 genes) and proteinases and inhibitors (4/4 genes) as demonstrated in the hierarchical cluster analysis (FIG. 6). A representative list of the genes differentially expressed at gestational week 38, along with the accession numbers and fold change is shown in Table I (below). Interestingly, there was a high degree of similarity concerning the identity as well as the fold change in expression comparing the genes obtained from the fetal and maternal placenta samples (FIG. 6, Table I). Hierarchical cluster analysis also illustrates co-regulated sets of related gene families, such as keratins, pregnancy-specific glycoproteins, ephrin ligands/Eph receptors, IGFBPs and heat shock proteins (FIG. 6). Most regulated genes were detected at late gestation stages, among those were potential candidates previously correlated with preeclampsia, such as EPAS-1/HIF-2α, PlGF, TIMP-1 and -2 were found to be upregulated (Table I). Reduced expression of TIMP-3, IGFBPs and decorin could also be confirmed by our microarray approach (Table I). Within the group of recently discussed genes we found deregulation of various ephrin receptors. While expression of EphA3, EphA4 was increased, EphB2 and EphA5 expression was diminished in preeclamptic placenta (Table I).

TABLE I

The accession number and fold change of the genes differentially expressed at gestational week 38. The values were calculated according to the method of variance stabilization. Only genes which were induced or repressed by at least 2.5 fold in one side of the placenta are included in the table. Accession numbers indicated the GenBank accession numbers. NA, not analyzed; f, fetal part/side of the placenta; m, maternal part/side of the placenta.

| Accession Number | Gene Name | Fold change (f) | (m) |
|---|---|---|---|
| A) cell and tissue structural dynamics | | | |
| X07695 | keratin 4 | 21.17 | 20.08 |
| M34481 | pregnancy-specific beta-1-glycoprotein 11 | 8.02 | 5.96 |
| U58516 | lactadherin precursor | NA | 3.66 |
| Y00796 | integrin alpha-L precursor | 3.4 | 2.54 |
| X72925 | desmocollin 1A/1B precursor | 2.91 | 2.7 |
| L41162 | collagen-type IX-alpha 3 | 2.94 | 2.49 |
| D00017 | annexin A2 | 3.6 | 2.31 |
| Y00503 | keratin 19 | 9.21 | 8.29 |
| X17097 | pregnancy-specific beta-1-glycoprotein 4 | 8.15 | 7.84 |
| X51521 | villin 2 | 6.67 | 3.85 |
| M82809 | annexin IV | 4.12 | 3.92 |
| X72012 | endoglin (Osler-Rendu-Weber syndrome 1) | 5.37 | 2.25 |
| U53204 | plectin 1 | 5.99 | 3.57 |
| S79867 | keratin 16 | 3.32 | 2.67 |
| X16609 | ankyrin 1 | 3.21 | 3.09 |
| X56134 | vimentin | −1.4 | −4.9 |
| AF052124 | osteopontin precursor | 1.43 | −5.61 |
| M14219 | decorin precursor | −1.32 | −5.51 |
| L07807 | dynamin 2 | −3.93 | −2.92 |
| D83542 | muscle cadherin precursor | −2.61 | −2.13 |
| X65873 | kinesin heavy chain | −2.65 | −2.01 |
| X52022 | collagen- type VI- alpha 3 | −2.57 | −2.06 |
| B) metabolism | | | |
| M14565 | cytochrome P450- subfamily XIA | 14.81 | 8.95 |
| U29344 | fatty acid synthase | 9.96 | 9.96 |
| M12938 | ferritin light chain | 3.54 | 3.03 |
| D44640 | adducin alpha | 4.25 | 2.85 |
| M28713 | NADH-cytochrome B5 reductase | 2.99 | 2.9 |
| J00140 | dihydrofolate reductase | 3.87 | 2.15 |
| U07151 | ADP-ribosylation factor like protein 3 | 2.79 | 2 |
| U90313 | glutathione-S-transferase (GST) homolog | 2.9 | 1.77 |
| M81600 | NADPH menadione oxidoreductase 1-dioxin-inducible | 3.29 | 2.15 |
| X02492 | 5'-nucleotidase (CD73) | 2.51 | 2.02 |
| M26880 | ubiquitin | 4.56 | 2.63 |
| J05459 | GST5- glutathione S-fransferase M3 (brain) | 3.25 | 2.16 |
| X02317 | superoxide dismutase 1 (soluble) | 2.92 | 2.18 |
| X15341 | cytochrome C oxidase subunit VIa polypeptide 1 | 3.94 | 3.42 |
| X15722 | glutathione reductase | 2.7 | 2.15 |
| D10522 | myristoylated alanine-rich protein kinase C substrate | 3.76 | 3.24 |
| AF080237 | protein disulfide isomerase A2 | −4.49 | −2.98 |
| U43431 | DNA topisomerase III alpha | −2.53 | −1.77 |
| C) regulation of gene expression | | | |
| AF048693 | forkhead (Drosophila)-like 7 | 35.16 | 25.3 |
| U11701 | LIM/Homeobox protein LHX2 | 21.71 | 15.17 |
| L25597 | paired box homeotic gene 2 | 16.4 | 18.57 |
| AF002228 | T-box transcription factor 3 TBX3 | 3.41 | 3.51 |
| U81984 | endothelial PAS domain 1 | 3.69 | 2.09 |

TABLE I-continued

The accession number and fold change of the genes differentially expressed at gestational week 38. The values were calculated according to the method of variance stabilization. Only genes which were induced or repressed by at least 2.5 fold in one side of the placenta are included in the table. Accession numbers indicated the GenBank accession numbers. NA, not analyzed; f, fetal part/side of the placenta; m, maternal part/side of the placenta.

| Accession Number | Gene Name | Fold change (f) | Fold change (m) |
|---|---|---|---|
| U34070 | C/EBP alpha- CCAAT/enhancer binding protein alpha | 6.21 | 6.3 |
| AJ005814 | homeobox A7 (HOXA7) | 7.58 | 3.56 |
| X52560 | CCAAT/enhancer binding protein (C/EBP)- delta | 3.08 | 2.61 |
| X63468 | FE-TFIIE general transcription factor | 7.32 | 7.73 |
| U67369 | disrupted in schizophrenia 1 protein | 5.27 | 3.76 |
| D43638 | core-binding factor- runt domain- alpha 2 (MTG8) | 2.54 | 3.18 |
| U02031 | sterol regulatory element binding transcription factor 2 | 3.39 | 2.52 |
| M35663 | interferon-induced dsRNA-activated protein kinase | 3.38 | 2.21 |
| L11672 | zinc finger protein 208 | 3.83 | 2.82 |
| M92299 | homeobox protein HOX-B5 | 2.67 | 2.3 |
| U16258 | NFKBIL2- IKBR | 4.37 | 2.49 |
| M97934 | signal transducer and activator of transcription 2 | 3.4 | 2.32 |
| L16794 | myocyte-specific enhancer factor 2D | 5.28 | 3 |
| D13318 | GA binding protein alpha chain | −3.25 | −2.5 |
| AF100318 | mitogen-activated protein kinase kinase 6 | −2.68 | −2.42 |
| D) intercellular communication | | | |
| M38451 | human growth hormone 2 | 8.99 | NA |
| L08187 | cytokine receptor (Epstein-Barr virus latent induced) | 19.97 | 12.64 |
| X54936 | placental growth factor | 4.24 | 5.46 |
| X02158 | erythropoietin | 4.5 | 3.68 |
| M21121 | small inducible cytokine A5 (RANTES) | 4.24 | 3.22 |
| M83941 | ephrin type A receptor 3 | 3.83 | 3.05 |
| AF055008 | granulin | 6.16 | 4.22 |
| M59818 | granulocyte colony stimulating factor receptor | 5.24 | 4.72 |
| X03663 | macrophage colony stimulating factor I receptor | 3.43 | 1.38 |
| M11730 | receptor protein-tyrosine kinase ERBB-2 precursor | 2.51 | 1.39 |
| J03634 | inhibin beta A | 5.19 | 3.12 |
| Y00815 | LAR- protein tyrosine phosphatase- receptor type- F | 2.53 | 2.79 |
| U50330 | bone morphogenetic protein 1 | 4.02 | 3.14 |
| X74979 | epithelial discoidin domain receptor 1 precursor | 3.11 | 2.56 |
| M24545 | small inducible cytokine A2 precursor | 3.84 | 2.41 |
| AJ006352 | ephrin type A4 related receptor | 2.82 | 1.87 |
| X01060 | CD7l receptor | 3.31 | 3.25 |
| M31145 | insulin-like growth factor binding protein 1 | NA | −10.13 |
| M35878 | insulin-like growth factor binding protein 3 | −2.26 | −5.76 |
| X95425 | EphA5,Hek7 | −1.13 | −3.73 |
| L06139 | angiopoietin 1 receptor precursor (TIE-2) | −3.83 | −2.49 |
| M10051 | insulin receptor | −2.75 | −1.66 |
| E) cell cycle and apoptosis | | | |
| M19645 | heat shock 70 kD protein 5 (glucose-regulated protein) | 7.56 | 4.84 |
| U33760 | S-phase kinase associated protein 1A | 4.58 | 2.83 |
| X12654 | chromosome condensation 1- RCC1 | 3.82 | 2.24 |
| U20536 | caspase 6 | 3.21 | 2.33 |
| X07270 | heat shock 90 kD protein A | −3.32 | −2.27 |
| F) proteinases and inhibitors | | | |
| AF023476 | disintegrin and metalloproteinase domain 12 (meltrin alpha) | 40.01 | 31.24 |
| J05593 | tissue inhibitor of metalloproteinase 2 (TIMP-2) | 12.5 | 9.02 |
| X03124 | tissue inhibitor of metalloproteinase 1 (TIMP-1) | 7.74 | 12.26 |
| AB010962 | metalloproteinase in the female reproductive tract-2 | 4.54 | 2.97 |

In order to verify the microarray data by an independent approach, semi-quantitative RT-PCR was performed for a number of genes that were highly upregulated and that have not yet been associated with preeclampsia, namely ADAM 12-S, EBI3, LIM and MIFR-2. For these selected genes the data of the semi-quantitative RT-PCR analysis supported the microarray data (FIG. 7A). For the most abundantly upregulated transcript representing the soluble form of ADAM 12-S, real-time PCR using the same RNA but in addition also RNA from distinct matched patient pairs confirmed our findings (FIG. 7B). In comparison to healthy placentas, ADAM 12-S mRNA was 5- to 45-fold induced in the fetal (FIG. 7B) as well as in the maternal part of preeclamptic placentas (data not shown).

Overexpression of ADAM 12-S in Placental Villi and Serum of Preeclamptic Patients: ADAM 12-S was the most upregulated transcript and represents the soluble form of a disintegrin metalloprotease discussed to be the IGFBP-protease (Loechel, F., J. W. Fox, G. Murphy, R. Albrechtsen, and U. M. Wewer. 2000. ADAM 12-S cleaves IGFBP-3 and IGFBP-5 and is inhibited by TIMP-3. *Biochem Biophys Res Commun* vol. 278, p. 511-515). Therefore, ADAM 12-S could be directly implicated in the pathophysiology of preeclampsia or could serve as an interesting candidate for diagnostics. Tissue sections from healthy and preeclamptic placenta samples were analysed by in situ hybridization. Weak expression of ADAM 12-S was found in the fibroblasts present in the villous mesenchyme, whereas high expression was seen in the syncytial knots of healthy placenta (FIGS. 4 and 5). Clearly, enhanced levels of ADAM 12-S transcript were detected in both fibroblasts and in the complete syncytiotrophoblast layer of preeclamptic placentas confirming our microarray and RT-PCR data (FIGS. 4 and 5).

Figure 3:
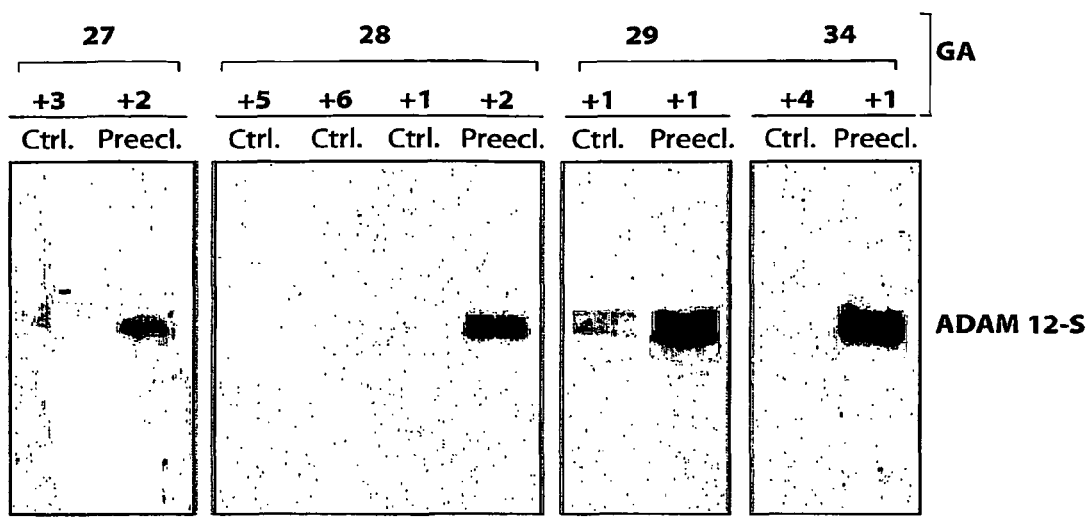
FIG. 3 Elevated ADAM-12S protein levels in sera from patients diagnosed with preeclampsia Immunoblot analysis of gestational age-matched sera obtained from healthy (ctrl.) and preeclamptic (preecl.) pregnant women using an ADAM-12S specific rabbit polyclonal antibody (Shi et al., 2000). Samples are arranged according to the gestational age (GA) when sera were collected, as indicated on the top (gestational week plus additional days of pregnancy).

As previously described, ADAM 12-S is found in the serum of pregnant females and its levels are increasing with gestational age (see FIG. 3 and Gilpin, B. J., F. Loechel, M. G. Mattei, E. Engvall, R. Albrechtsen, and U. M. Wewer. 1998. A novel, secreted form of human ADAM 12 (meltrin alpha) provokes myogenesis in vivo. *J Biol Chem vol.* 273, p. 157-166). To investigate whether ADAM 12-S protein levels are still further enhanced in the serum of preeclamptic patients, sera from non-pregnant and gestational age-matched healthy and preeclamptic women were analyzed by Western blot analysis using the polyclonal rabbit antibody rb122. These patient pairs were not identical to those analysed by microarray or RT-PCR analysis and therefore represent an independent study approach (compare FIG. 8). The 68 kDa protease was easily detected in the sera of both groups, however, it was significantly increased in the serum of patients diagnosed with preeclampsia (FIG. 3).

---

The invention claimed is:

1. A method for diagnosing a pregnant woman at increased risk of preeclampsia comprising the steps of:
   a) obtaining a serum or plasma sample from a the woman in the second or third trimester of pregnancy;
   b) contacting the sample with an antibody that specifically binds a marker, wherein the marker is a protein consisting of the amino acid sequence as presented in SEQ ID NO: 4;
   c) determining the amount of the marker in the sample;
   d) comparing the determined amount of the marker with a reference amount derived from gestation age matched healthy women; and
   e) establishing a diagnosis based on the result of step d), wherein a higher determined amount of the marker as compared to the reference amount of the marker is indicative of preeclampsia.

2. The method of claim 1, wherein the marker according to claim 1 is used in conjunction with a diagnostic agent for the measurement of expression of any of the proteins selected from the group consisting of:
   a) EPAS-1/HIF-2α;
   b) neurokinin B;
   c) TIMP-1;
   d) VEGFR-1;
   e) VEGF;
   f) IGFBP-1;
   g) IGFBP-3;
   ह) matrix metalloproteinase-2;
   i) leptin;
   j) PAI-1;
   k) IGF-1;
   l) angiopoetin-2;
   m) decorin;
   n) PlGF;
   o) HLA-G;
   p) HB-EGF;
   q) TGF-β3;
   r) MIFR-2;
   s) LIM; and
   t) EBI3;
and/or diagnostic tools for the measurement of blood pressure or protein content of the urine.

3. A method of diagnosing a pregnant woman at increased risk of a disease selected from the group consisting of eclampsia and HELLP syndrome, comprising the steps of:
   a) obtaining a serum or plasma sample from the pregnant woman in the second or third trimester of pregnancy;
   b) contacting the sample with an antibody that specifically binds a marker, wherein the marker is a protein consisting of the amino acid sequence as presented in SEQ ID NO: 4;
   c) determining the amount of the marker in the sample;
   d) comparing the determined amount of the marker with a reference amount derived from gestation age matched healthy women; and e) establishing a diagnosis based on the result of step d), wherein a higher determined amount of the marker as compared to the reference amount of the marker is indicative of an increased risk of at least one of eclampsia and HELLP syndrome.

4. The method of claim 3, wherein the marker according to claim 3 is used in conjunction with a diagnostic agent for the measurement of expression of any of the proteins selected from the group consisting of:
a) EPAS-1/HIF-2α;
b) neurokinin B;
c) TIMP-1;
d) VEGFR-1;
e) VEGF;
f) IGFBP-1;
g) IGFBP-3;
h) matrix metalloproteinase-2;
i) leptin;
j) PAI-1;
k) IGF-1;
l) angiopoetin-2;
m) decorin;
n) PlGF;
o) HLA-G;
p) HB-EGF;
q) TGF-β3;
r) MIFR-2;
s) LIM; and
t) EBI3;
and/or diagnostic tools for the measurement of blood pressure or protein content of the urine.

* * * * *

UNITED STATES PATENT AND TRADEMARK OFFICE
CERTIFICATE OF CORRECTION

PATENT NO. : 7,842,464 B2  
APPLICATION NO. : 10/576266  
DATED : November 30, 2010  
INVENTOR(S) : Gack et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 515 days.

Signed and Sealed this

Thirty-first Day of May, 2011

David J. Kappos
*Director of the United States Patent and Trademark Office*